US011167310B2

(12) United States Patent
Clark

(10) Patent No.: US 11,167,310 B2
(45) Date of Patent: Nov. 9, 2021

(54) SEALING ASSEMBLY FOR FORMING SEALANT COATING ON A FASTENER, THE SEALING ASSEMBLY COMPRISING A LIGHT GENERATOR AND A FORMING CUP ASSOCIATED WITH THE LIGHT GENERATOR

(71) Applicant: The Boeing Company, Chicago, IL (US)

(72) Inventor: Kelly L. Clark, Seattle, WA (US)

(73) Assignee: The Boeing Company, Chicago, IL (US)

( * ) Notice: Subject to any disclaimer, the term of this patent is extended or adjusted under 35 U.S.C. 154(b) by 421 days.

(21) Appl. No.: 14/711,123

(22) Filed: May 13, 2015

(65) Prior Publication Data

US 2016/0332189 A1   Nov. 17, 2016

(51) Int. Cl.
*B05D 3/06* (2006.01)
*B05C 11/10* (2006.01)
*B05C 17/10* (2006.01)
*B05C 17/005* (2006.01)
*B05C 9/12* (2006.01)
(Continued)

(52) U.S. Cl.
CPC .............. *B05D 1/00* (2013.01); *B05C 5/0225* (2013.01); *B05C 9/12* (2013.01); *B05C 9/14* (2013.01); *B05C 11/1028* (2013.01); *B05C 11/1034* (2013.01); *B05C 17/00516* (2013.01); *B05C 17/10* (2013.01); *B05D 3/067* (2013.01); *B29C 41/00* (2013.01); *F21V 15/01* (2013.01); *F21V 17/16* (2013.01); *F21V 17/164* (2013.01); *F21V 23/005* (2013.01); *F26B 3/28* (2013.01); *A61C 19/004* (2013.01); *A61N 2005/0652* (2013.01); *B05D 2258/00* (2013.01); *B29C 35/0888* (2013.01); *B29C 39/10* (2013.01); *B29C 2035/0827* (2013.01); *B64C 1/12* (2013.01);
(Continued)

(58) Field of Classification Search
CPC ....... B05C 9/12; B05C 9/14; B05C 17/00546; F16B 33/06; F16B 33/004; B29C 35/08; B29C 71/04; B29C 2035/8027; F21V 15/012
USPC ........ 250/492.1, 493.1; 313/146; 362/217.01
See application file for complete search history.

(56) References Cited

U.S. PATENT DOCUMENTS 3,470,787 A * 10/1969 Mackie ................. F16B 33/004
264/250
4,100,860 A   7/1978 Gablin et al.
(Continued)

OTHER PUBLICATIONS

"Define Housing at Dictionary.com", Jan. 10, 2019, Dictionary. com,LLC https://www.dictionary.com/browse/housing, p. 1, 2019.*
(Continued)

*Primary Examiner* — Karl Kurple
(74) *Attorney, Agent, or Firm* — Yee & Associates, P.C.

(57) ABSTRACT

A method and apparatus for forming a sealant coating on a fastener are provided. The apparatus comprises a light generator, a light housing, and a forming cup. The light generator is configured to generate light having a number of characteristics that cures the sealant coating on the fastener. The light housing surrounds the light generator. The forming cup is removably connected to the light housing. The forming cup has an internal cavity with an inner mold line complementary to an outer mold line for the sealant coating.

23 Claims, 17 Drawing Sheets

(51) Int. Cl.
*F21V 15/01* (2006.01)
*F21V 23/00* (2015.01)
*B05D 1/00* (2006.01)
*B29C 41/00* (2006.01)
*B05C 5/02* (2006.01)
*F21V 17/16* (2006.01)
*F26B 3/28* (2006.01)
*B05C 9/14* (2006.01)
*F16B 33/00* (2006.01)
*B29C 39/10* (2006.01)
*B64C 1/12* (2006.01)
*A61N 5/06* (2006.01)
*E01C 23/06* (2006.01)
*B29C 35/08* (2006.01)
*F21Y 115/10* (2016.01)
*A61C 13/15* (2006.01)

(52) U.S. Cl.
CPC ............. *E01C 23/03* (2013.01); *F16B 33/004* (2013.01); *F21Y 2115/10* (2016.08)

(56) References Cited

U.S. PATENT DOCUMENTS

| | | | |
|---|---|---|---|
| 4,476,995 A | 10/1984 | Bellino et al. | |
| 4,519,974 A | 5/1985 | Bravenec et al. | |
| 4,521,456 A * | 6/1985 | Hanson | B05C 17/002 118/410 |
| 4,522,594 A * | 6/1985 | Stark | A61C 19/004 433/141 |
| 4,632,944 A * | 12/1986 | Thompson | C09J 4/00 411/258 |
| 4,772,093 A * | 9/1988 | Abele | A61B 1/00096 385/117 |
| 4,826,380 A * | 5/1989 | Henry | B64D 45/02 156/229 |
| 4,971,745 A | 11/1990 | Ferenc et al. | |
| 5,028,330 A * | 7/1991 | Caronia | B01D 27/005 156/275.5 |
| 5,275,679 A * | 1/1994 | Rojek | B29C 65/60 156/250 |
| 5,322,381 A * | 6/1994 | Argo, II | B65D 47/06 222/566 |
| 5,394,449 A | 2/1995 | Johnson et al. | |
| 5,608,290 A * | 3/1997 | Hutchisson | H05B 47/155 315/200 A |
| 5,698,866 A * | 12/1997 | Doiron | A61N 5/062 257/717 |
| 5,759,032 A * | 6/1998 | Bartel | A61C 19/004 385/43 |
| 6,033,223 A * | 3/2000 | Narusawa | A61C 5/00 433/226 |
| 6,200,134 B1 * | 3/2001 | Kovac | A61C 19/004 433/29 |
| 6,331,111 B1 * | 12/2001 | Cao | A61C 19/004 362/119 |
| 6,402,511 B1 * | 6/2002 | Calderwood | A61B 1/00142 433/116 |
| 6,702,576 B2 * | 3/2004 | Fischer | A61C 19/004 433/29 |
| 6,953,339 B1 * | 10/2005 | Daffurn | A61C 19/004 433/29 |
| 7,671,346 B2 * | 3/2010 | Siegel | B05D 3/067 118/620 |
| 7,967,587 B2 * | 6/2011 | Bradley | B05C 9/14 249/157 |
| 8,002,546 B2 * | 8/2011 | Viscomi | A61C 3/00 433/141 |
| 9,066,777 B2 * | 6/2015 | Gill | F21V 23/06 |
| 9,228,604 B2 * | 1/2016 | Dobbin | B64D 45/02 |
| 9,416,811 B2 * | 8/2016 | Dobbin | B64D 45/02 |
| 9,650,150 B2 * | 5/2017 | Zook | B64D 37/06 |
| 9,653,670 B2 * | 5/2017 | Illek | H01L 33/64 |
| 9,707,590 B2 * | 7/2017 | Jurcevic | B05C 17/0052 |
| 2002/0073921 A1 * | 6/2002 | Russell | B05D 3/067 118/620 |
| 2003/0133203 A1 * | 7/2003 | McLean | G02B 7/02 359/708 |
| 2003/0162143 A1 * | 8/2003 | Fischer | A61C 19/004 433/29 |
| 2004/0043351 A1 * | 3/2004 | Logan | A61C 19/004 433/29 |
| 2004/0090794 A1 * | 5/2004 | Ollett | A61C 19/004 362/555 |
| 2004/0134603 A1 * | 7/2004 | Kobayashi | B29C 65/1406 156/272.8 |
| 2004/0245677 A1 * | 12/2004 | Marple | B29C 33/36 264/496 |
| 2005/0104946 A1 * | 5/2005 | Siegel | B41F 23/0409 347/102 |
| 2005/0116235 A1 * | 6/2005 | Schultz | H01L 24/48 257/79 |
| 2005/0195598 A1 * | 9/2005 | Danes | A61L 9/037 362/231 |
| 2005/0236586 A1 * | 10/2005 | Hartung | G02B 6/4298 250/492.3 |
| 2006/0109649 A1 * | 5/2006 | Ducharme | H05B 33/0857 362/231 |
| 2006/0274421 A1 * | 12/2006 | Okamitsu | A61C 13/001 359/618 |
| 2007/0054230 A1 * | 3/2007 | Brezniak | A44C 15/007 433/24 |
| 2007/0241478 A1 * | 10/2007 | Buckley | B29B 11/16 264/257 |
| 2008/0057463 A1 * | 3/2008 | Wong | A61K 6/884 433/29 |
| 2008/0134971 A1 * | 6/2008 | Bradley | B05C 9/14 118/641 |
| 2009/0126628 A1 * | 5/2009 | Brendel | B05D 3/0209 118/708 |
| 2009/0208894 A1 * | 8/2009 | Orloff | A61C 19/004 433/29 |
| 2009/0217868 A1 * | 9/2009 | Caseteuble | B05C 17/00503 118/300 |
| 2010/0130636 A1 * | 5/2010 | Karunaratne | B05D 3/067 522/153 |
| 2013/0092847 A1 * | 4/2013 | Childers | G02B 6/44 250/492.1 |
| 2013/0229795 A1 * | 9/2013 | Wang | F21V 19/04 362/224 |
| 2013/0341531 A1 * | 12/2013 | Bonham | B05C 9/12 250/492.1 |
| 2014/0261956 A1 * | 9/2014 | Wiseman | A47L 13/08 156/60 |
| 2015/0037535 A1 * | 2/2015 | Akimoto | C08F 2/44 428/141 |
| 2016/0008848 A1 * | 1/2016 | Larson | B05D 3/067 427/8 |
| 2016/0016192 A1 * | 1/2016 | Yang | H01L 33/005 438/29 |
| 2016/0068274 A1 * | 3/2016 | Zook | B64D 45/02 16/108 |
| 2017/0157637 A1 * | 6/2017 | Jurcevic | B05C 17/0052 |
| 2017/0190442 A1 * | 7/2017 | Zook | B64D 45/02 |
| 2018/0050364 A1 * | 2/2018 | Larrabee | F16B 39/021 |
| 2019/0195266 A1 * | 6/2019 | Pillay | F16B 33/004 |

OTHER PUBLICATIONS

Song, "In-Situ Injection Molded Fastener Cap Seal Using Thermoplastic Elastomer Materials," U.S. Appl. No. 14/543,253, filed Nov. 17, 2014, 16 pages.

"Sealants and Sealing Introduction," MLevel3.com, Aircraft Sealants—Information for maintenance engineer students, pp. 1-21, accessed Jan. 3, 2012. http://www.mlevel3.com/BCIT/Sealants.htm.

(56) References Cited

OTHER PUBLICATIONS

Wicklund, "Policy on Issuance of Special Conditions and Exemptions Related to Lightning Protection of Fuel Tank Structure," Federal Aviation Administration Memorandum, Policy Reference AC25.981-1C, May 2009, pp. 1-16.
"Flying High," ASI Adhesives Magazine, Sep. 2005, pp. 1-3.
Gaw, "Foamed Energy Absorptive Fastener Seal Cap," U.S. Appl. No. 13/363,853, filed Feb. 1, 2012, 36 pages.

* cited by examiner

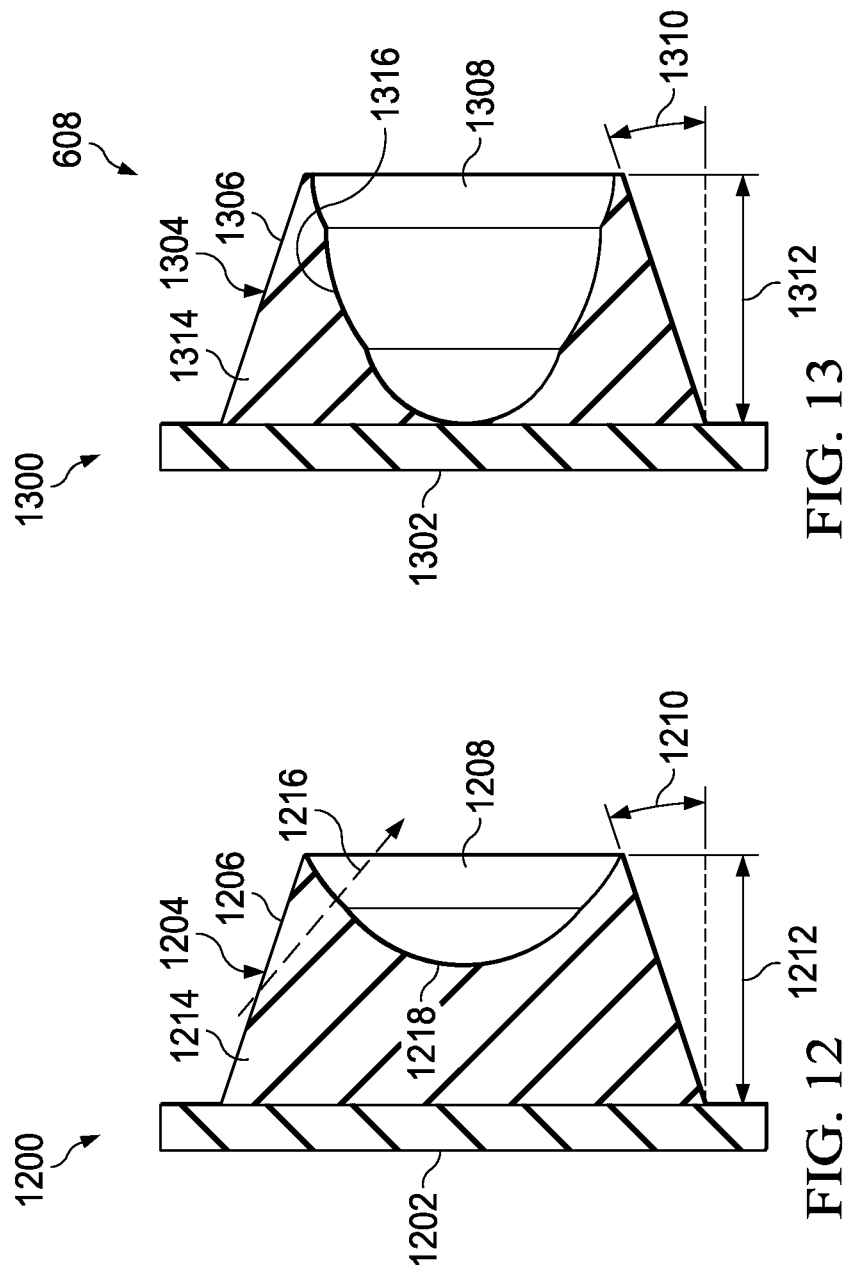

SEALING ASSEMBLY FOR FORMING SEALANT COATING ON A FASTENER, THE SEALING ASSEMBLY COMPRISING A LIGHT GENERATOR AND A FORMING CUP ASSOCIATED WITH THE LIGHT GENERATOR

BACKGROUND INFORMATION

1. Field

The present disclosure relates generally to fuel tanks. In particular, the present disclosure relates to a method and apparatus for sealing fasteners within the interior of a fuel tank.

2. Background

Fuel tanks in aircraft are often integral structures to the aircraft. For example, the wing structure of an aircraft may be sealed. The internal cavities of the sealed wing structure may be used as a fuel tank. These types of wings are also referred to as "wet wings".

With a wet wing, components, such as fasteners, hoses, tubing, or other components that extend into the wing, can be sealed to exclude the outside from the inside, or covered to reduce or eliminate the buildup of electrical charge on conductive surfaces. These components can extend through structures within the fuel tank, such as stringers, or between bays of the fuel tank via holes in the structures forming the fuel tank, such as ribs or other supporting structures. In conventional fuel tanks made from metal, components and the holes through which they extend may be sealed to reduce leaking or seepage of the fuel tank formed in the wing. In composite structures, the sealing of metal surfaces and the holes that penetrate the structure may have a number of purposes including the reduction of fuel leakage, with respect to fuel leaking out of the tank, the reduction of other fluids entering or exiting the fuel tank, the coverage of metal components that can have a propensity to accumulate electrical charge, or the prevention of galvanic corrosion.

Components, such as metallic fasteners, may be sealed. Sealant in the form of seal caps may cover these fasteners. A "seal cap" is a structure that covers an end of a metallic component. The metallic component may be a fastener. The end may be the head fastener or the threaded end of the fastener with a nut. The fastener may be, for example, a bolt, a screw, or some other type of fastener.

For example, a seal cap may be attached to the end of a fastener that extends into the interior of the fuel tank. This seal cap is configured to provide a seal against the flow of fuel out of the fuel tank. The seal cap may also reduce or eliminate the accumulation of electrical charge on the surface of the exposed fastener.

Seal caps are often comprised of materials that retain sealing properties when submerged in fuel and/or when left dry for different periods of time. For example, molded polymeric seal caps may be used in fuel tanks for aircraft. These types of seal caps may fit over the protruding end of a fastener on the interior of the fuel tank. Sealants may be placed into the seal caps prior to the seal caps being placed on the fastener. The sealant may be in the form of a plastic forming material.

For example, a seal cap may have an interior that is partially filled with an uncured sealant. This seal cap with the sealant is then pressed into place on the fastener. When in this position, excess sealant extrudes from around the bottom of the cap. This sealant may be blended around and onto the exterior of the cap. The sealant is then allowed to cure to form the final sealant material.

However, installing molded seal caps may take an undesirable amount of time. For example, molded seal caps may be placed over fasteners manually. Manual installation may take an undesirable amount of time. Further, molded seal caps may be manually inspected for voids prior to installation over fasteners. Yet further, blending extruded sealant may be performed manually and require training to meet desired tolerances.

Therefore, it would be desirable to have a method and apparatus that take into account at least some of the issues discussed above, as well as possibly other issues.

SUMMARY

In one illustrative embodiment, an apparatus for forming a sealant coating on a fastener is provided. The apparatus comprises a light generator, a light housing, and a forming cup. The light generator is configured to generate light having a number of characteristics that cures the sealant coating on the fastener. The light housing surrounds the light generator. The forming cup is removably connected to the light housing. The forming cup has an internal cavity with an inner mold line complementary to an outer mold line for the sealant coating.

A further illustrative embodiment of the present disclosure provides an apparatus for forming sealant coating on a fastener. The apparatus comprises a light generator and a forming cup. The light generator is configured to generate light that has a number of characteristics that cures the sealant coating on a fastener. The forming cup is formed of a material substantially transparent to the light generated by the light generator. The forming cup has a shape to direct the light to a sealant contained within an internal cavity of the forming cup.

A yet further illustrative embodiment of the present disclosure provides a method for applying and curing a sealant coating on a fastener. Sealant is held within an interior cavity of a forming cup. Light is generated using a light generator. The light generated by the light generator is directed into the sealant using the forming cup. The light cures the sealant coating on the fastener.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives, and features thereof will best be understood by reference to the following detailed description of an illustrative embodiment of the present disclosure when read in conjunction with the accompanying drawings, wherein:

FIG. 12 is an illustration of a side cross-sectional view of a forming cup in accordance with an illustrative embodiment;

FIG. 13 is an illustration of a side cross-sectional view of a forming cup in accordance with an illustrative embodiment;

DETAILED DESCRIPTION

The different illustrative embodiments recognize and take into account one or more considerations. For example, the illustrative embodiments recognize and take into account that currently used sealing systems may employ seal caps that are configured to reduce the transfer of energy into a fuel tank system caused by an electromagnetic event. The transfer of energy may involve a spark, a static discharge, a gas under pressure, a heated gas, a mechanical force, or some other transfer of energy that may be undesirable within a fuel tank system.

The illustrative embodiments also recognize and take into account that seal caps may add an undesired amount of time to manufacturing the structure. Yet further, the illustrative embodiments recognize and take into account that a fuel tank system may have restricted space. Movement within the fuel tank system may be limited by the size of the fuel tank system. Further, the distances between a number of fasteners in the fuel tank system may be small. The illustrative embodiments recognize and take into account that an apparatus for applying sealant in a fuel tank system should be sufficiently compact to move within the fuel tank system.

Thus, the illustrative embodiments provide a method and apparatus for reducing manufacturing time for sealing fasteners in a fuel tank system, reducing a transfer of energy in a fuel tank system, or a combination of the two.

Figure 1:
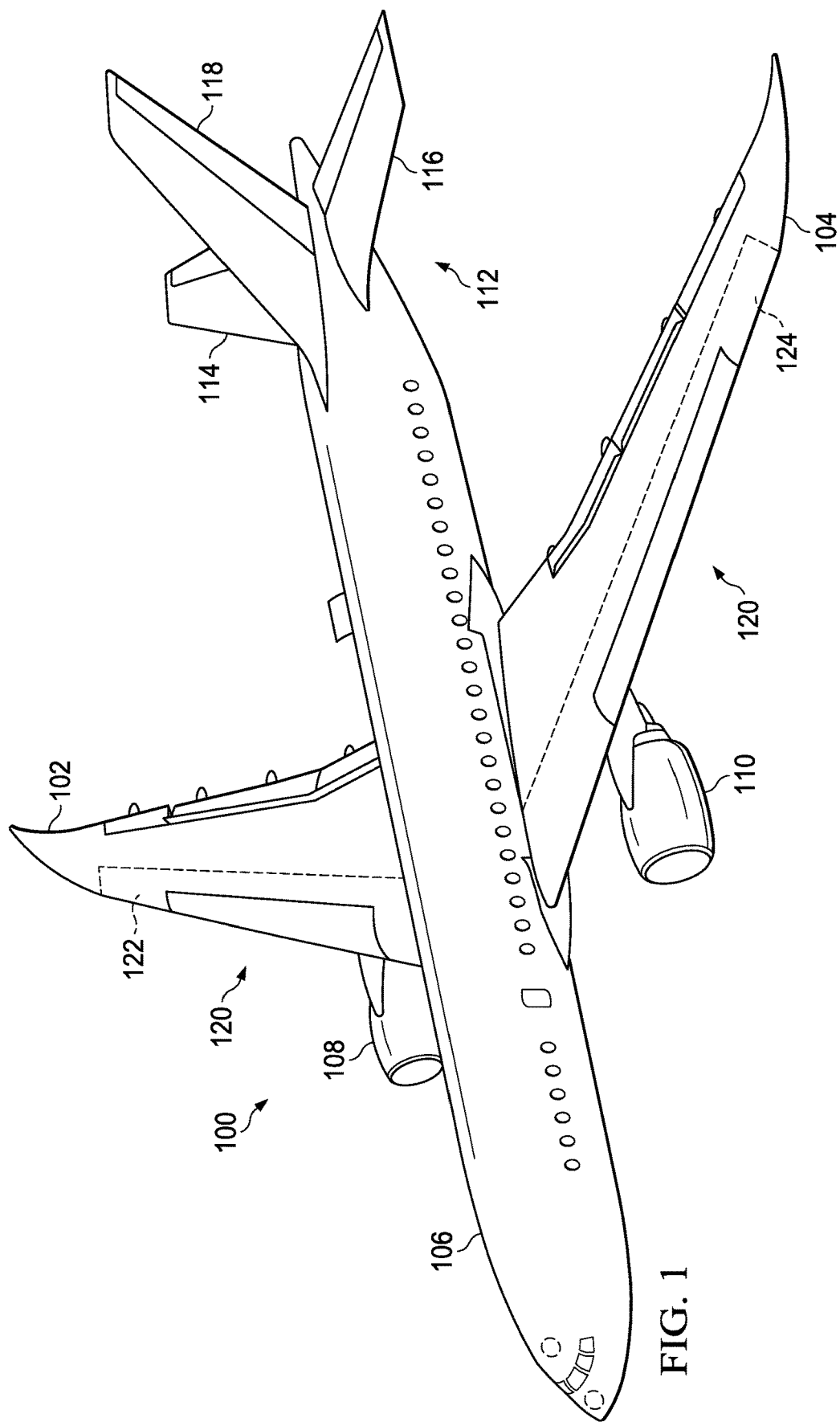
FIG. 1 is an illustration of an aircraft in accordance with an illustrative embodiment.

With reference now to the figures and, in particular, with reference to FIG. 1, an illustration of an aircraft is depicted in accordance with an illustrative embodiment. In this illustrative example, aircraft 100 has wing 102 and wing 104 attached to body 106. Aircraft 100 includes engine 108 attached to wing 102 and engine 110 attached to wing 104.

Body 106 has tail section 112. Horizontal stabilizer 114, horizontal stabilizer 116, and vertical stabilizer 118 are attached to tail section 112 of body 106. As depicted, aircraft 100 also includes fuel tank system 120. As depicted, fuel tank system 120 includes fuel tank 122 and fuel tank 124.

Fuel tank 122 is located in wing 102 and fuel tank 124 is located in wing 104 in fuel tank system 120. In these illustrative examples, fuel tank 122 and fuel tank 124 are formed by sealing structures inside of wing 102 and wing 104, respectively. A sealing system for fasteners in fuel tank system 120 may be implemented in accordance with an illustrative embodiment.

Figure 2A:
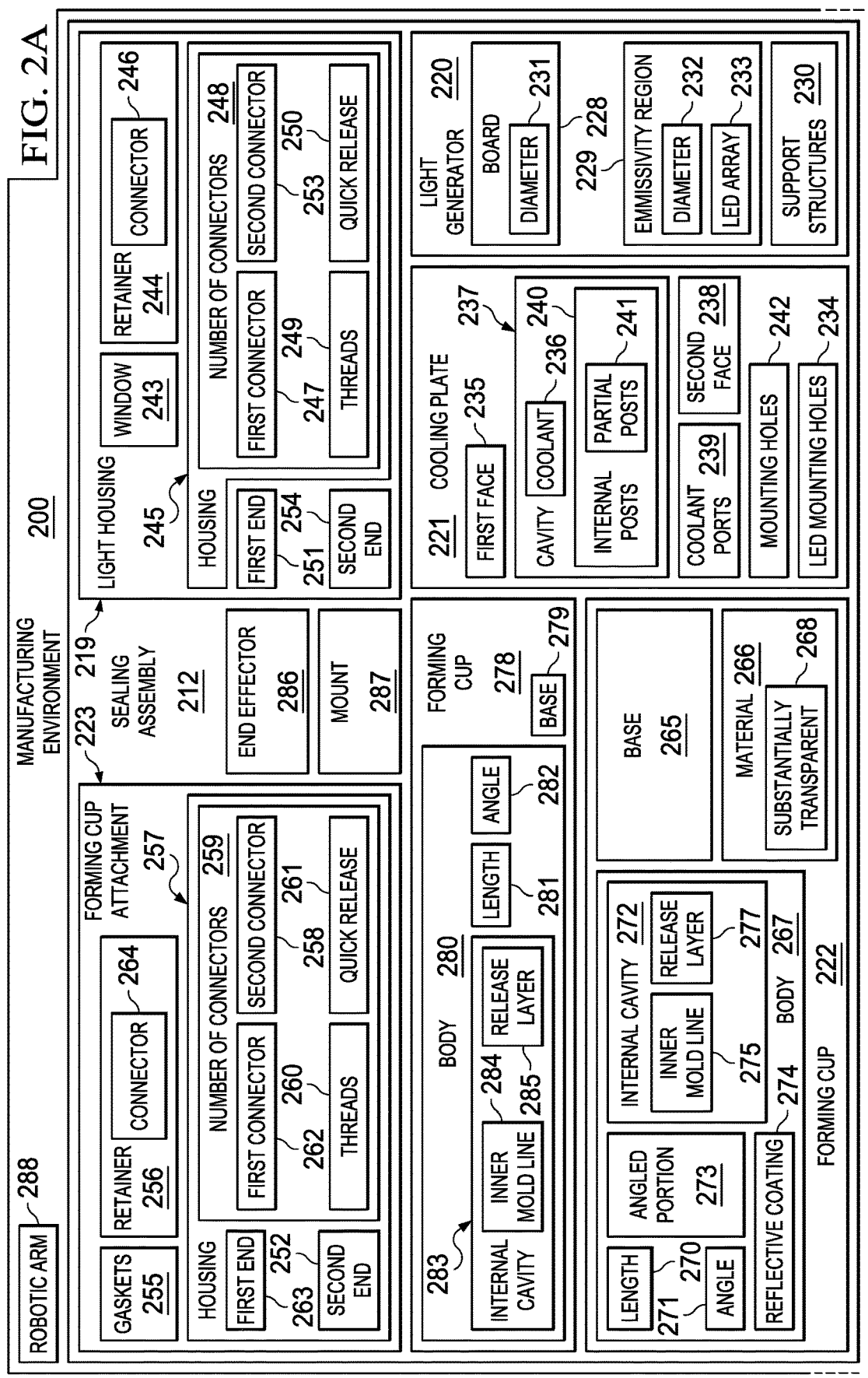
FIGS. 2A and 2B are an illustration of a block diagram of a manufacturing environment in accordance with an illustrative embodiment.
Figure 2B:
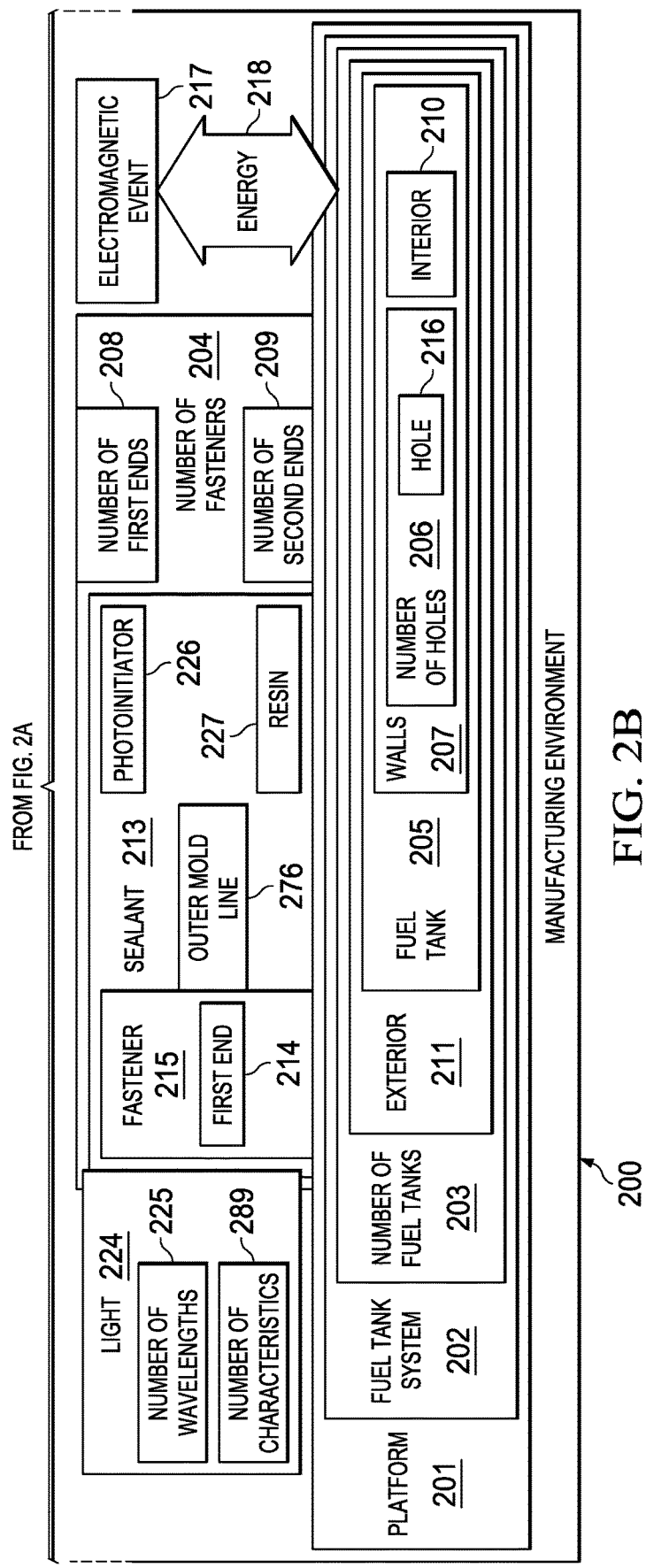

With reference next to FIGS. 2A and 2B, an illustration of a block diagram of a manufacturing environment is depicted in accordance with an illustrative embodiment. In this illustrative example, manufacturing environment 200 may be used to seal fasteners in platform 201. Aircraft 100 of FIG. 1 is an example of a physical implementation of platform 201 in FIGS. 2A and 2B.

Platform 201 includes fuel tank system 202. Fuel tank system 120 in FIG. 1 is an example of an implementation for fuel tank system 202 in FIGS. 2A and 2B. Fuel tank system 202 includes number of fuel tanks 203. As used herein, a "number of," when used with reference to items, means one or more items. For example, "number of fuel tanks 203" is one or more fuel tanks. Fuel tank 122 and fuel tank 124 in FIG. 1 are examples of fuel tanks that may be in number of fuel tanks 203. A fuel tank in number of fuel tanks 203 also may be in locations other than in wing 102 and wing 104 of aircraft 100. For example, a fuel tank may be located in body 106 of aircraft 100.

In these illustrative examples, number of fasteners 204 is installed in fuel tank 205 in number of fuel tanks 203. In particular, number of fasteners 204 may be installed in number of holes 206 formed in structures 207. Structures 207 may be structures forming or supporting fuel tank 205. Structures 207 may include at least one of a number of ribs, a number of spars, a number of skins, or other structures. Number of fasteners 204 may have a large quantity of fasteners. For example, number of fasteners 204 may include between 20,000 and 80,000 fasteners. When number of fasteners 204 includes a large quantity of fasteners, even small increases in time for an individual fastener related to manufacturing, sealing, or inspecting may increase overall manufacturing time by a large amount of time.

Number of fasteners 204 has number of first ends 208 and number of second ends 209. Number of first ends 208 extends into interior 210 of fuel tank 205. Number of second ends 209 is on exterior 211 of fuel tank 205.

In this illustrative example, sealing assembly 212 may be used in fuel tank 205 in number of fuel tanks 203. In particular, sealing assembly 212 may be used to seal number of fasteners 204 installed in fuel tank 205. More specifically, sealing assembly 212 may be used to seal number of holes 206 in structures 207 of fuel tank 205 with number of fasteners 204 installed in number of holes 206. Sealing assembly 212 may apply and cure sealant 213 to first end 214 of fastener 215. As sealant 213 coats first end 214 of fastener 215, sealant 213 may be also referred to as a sealant coating.

The illustrative embodiments recognize and take into account that movement within fuel tank system 202 during assembly may be restricted. Movement within fuel tank system 202 may be limited by the position of structures 207 such as a number of ribs, a number of spars, or other structures. The illustrative embodiments recognize and take into account that sealing assembly 212 in fuel tank system 202 should be sufficiently compact to move within fuel tank system 202 to apply sealant to number of fasteners 204.

Further, the distances between number of fasteners 204 in fuel tank system 202 may be small. Thus, the illustrative embodiments recognize and take into account that sealing assembly 212 should be sufficiently compact to be positioned relative to fastener 215 to apply and cure sealant 213. For example, sealing assembly 212 should be sufficiently compact to apply and cure sealant 213 to fastener 215 without undesirably impacting neighboring fasteners of number of fasteners 204.

As depicted, sealant 213 is configured to cover first end 214 of fastener 215 in number of fasteners 204. Sealant 213 forms a barrier between first end 214 of fastener 215 and interior 210 of fuel tank 205.

First end 214 of fastener 215 is an end within number of first ends 208 that extends into interior 210 of fuel tank 205 from structures 207. In these illustrative examples, fastener 215 is installed in hole 216 within number of holes 206 in fuel tank 205.

In the illustrative examples, sealant 213 is configured to reduce effects resulting from electromagnetic event 217. In particular, sealant 213 may be configured to reduce the transfer of energy 218 into or within interior 210 of fuel tank 205. The transfer of energy 218 may be into interior 210 of fuel tank 205 from current caused by electromagnetic event 217. The transfer of energy 218 may be within interior 210 of fuel tank 205 from electrostatic charge that builds up on metal components within interior 210 of fuel tank 205.

In the illustrative examples, electromagnetic event 217 may be, for example, without limitation, a lightning strike, electrostatic discharge, or other types of discharge for platform 201. Electromagnetic event 217 may transfer energy 218 to platform 201.

In these illustrative examples, energy 218 may take a number of different forms. For example, energy 218 may be at least one of a spark, an electrostatic discharge, heat, a mechanical force, a moving particle, or some other form of energy that may be undesirable within interior 210 of fuel tank 205. As used herein, the phrase "at least one of," when used with a list of items, means different combinations of one or more of the listed items may be used and only one of each item in the list may be needed. For example, "at least one of item A, item B, and item C" may include, without limitation, item A, or item A and item B. This example also may include item A, item B, and item C, or item B and item C.

In an illustrative example, energetic particles may originate from one or more of number of first ends 208 of number of fasteners 204 in response to electromagnetic event 217. In the illustrative examples, sealant 213 is configured to reduce and/or prevent energy 218 from being transferred into or within interior 210 of fuel tank 205. Sealant 213 is configured to contain energy 218, absorb energy 218, or a combination of the two. By containing energy 218, absorbing energy 218, or a combination of the two, the amount of energy 218 reaching interior 210 of fuel tank 205 may be reduced, prevented, or both. In these illustrative examples, containing energy 218 means that the amount of energy 218 reaching interior 210 of fuel tank 205 is reduced, prevented, or reduced and prevented.

Sealant 213 may be formed of polymeric material such as a polysulfide and/or other suitable plastic materials. In the illustrative examples, the material of sealant 213 may be selected as one that does not retain undesired amounts of electric charges. The material of sealant 213 may be selected as one that is electrostatically conductive.

As another example, the material of sealant 213 may be selected as having properties configured to contain energy 218 in the form of thermal energy. The thermal energy may be, for example, in the form of a spark or heated gas.

The material of sealant 213 may be selected for desirable inspection or application properties. For example, the material of sealant 213 may be selected such that sealant 213 is substantially transparent after curing. When sealant 213 is substantially transparent after curing, sealant 213 may be visually inspected for voids. Further, the material of sealant 213 may be selected such that sealant 213 may be self-leveling when sealant 213 is applied to at least one of fastener 215 or structures 207.

Sealing assembly 212 may apply and cure sealant 213 to first end 214 of fastener 215. Sealing assembly 212 includes light housing 219, light generator 220, cooling plate 221, forming cup 222, and forming cup attachment 223. Light housing 219 may cure sealant 213. Specifically, light generator 220 may generate light 224 having number of wavelengths 225. Light 224 may activate photoinitiator 226 to start curing resin 227 of sealant 213.

Light generator 220 includes board 228, emissive region 229, and support structures 230. Board 228 has diameter 231. Emissive region 229 has diameter 232 which is smaller than diameter 231. Diameter 232 may be any desirable size. In some illustrative examples, diameter 232 is between one inch and three inches. In some illustrative examples, diameter 232 may be about an inch and a half. Emissive region 229 includes light emitting diode (LED) array 233. Light emitting diode array 233 may be densely packed. Light emitting diode array 233 has a desired density of packing.

In some illustrative examples, light emitting diode array 233 may be arranged in a rectangular arrangement to form a densely packed array. Light emitting diode array 233 may be associated with board 228 in any desirable fashion. For example, light emitting diode array 233 may be fastened to board 228 using a number of fasteners. In some illustrative examples, a thermal paste may be positioned between light emitting diode array 233 and board 228 when light emitting diode array 233 is fastened to board 228. The thermal paste may provide thermal contact between light emitting diode array 233 and board 228. In some illustrative examples, light emitting diode array 233 may be adhered to board 228 using a thermally conductive adhesive.

Support structures 230 may support the performance of light emitting diode array 233. For example, support structures 230 may provide at least one of signals, electricity, or other desirable types of support to light emitting diode array 233. Support structures 230 may be positioned around the perimeter of board 228. For example, support structures 230 may be positioned on board 228 outside of emissive region 229. Support structures 230 may be around a periphery of light emitting diode array 233.

Light emitting diode array 233 may be configured to generate number of wavelengths 225 of light 224 based on the selection of sealant 213. Alternatively, sealant 213 may be selected based on number of wavelengths 225 of light 224 to be generated by light emitting diode array 233. Number of wavelengths 225 may include at least one of a UV wavelength or a visible wavelength. Number of wavelengths 225 may be selected based on the wavelength absorbance of at least one of resin 227 or photoinitiator 226. Shorter wavelengths tend to cause surface cure and a slower overall cure of sealant 213. Longer wavelengths may give a more uniform cure of sealant 213. Number of wavelengths 225 may be selected such that number of wavelengths 225 is not absorbed by resin 227.

Support structures 230 may control light 224 emitted by light emitting diode array 233. For example, support structures 230 may control the level of power at which light emitting diode array 233 performs. For example, light emitting diode array 233 may operate at less than 100 percent power. Over time, the intensity of light emitting diode array 233 may decrease. As the intensity of light emitting diode array 233 decreases, support structures 230 may increase the power supplied to light emitting diode array 233.

In some illustrative examples, light emitting diode array 233 may have a plurality of channels. Support structures 230 may be used to individually control each channel of light emitting diode array 233. For example, LEDs in a first channel of light emitting diode array 233 may be controlled to be more intense than LEDs in a second channel in light emitting diode array 233. The plurality of channels may be designed based on the geometry of sealant 213, the size of board 228, or the thermal characteristics of sealing assembly 212.

Light emitting diode array 233 may generate heat as well as light 224. Cooling plate 221 may provide cooling to light generator 220. Cooling plate 221 may be connected to light generator 220 and a liquid coolant supply system. Cooling plate 221 may be directly connected to light generator 220. Light generator 220 may be directly connected to cooling plate 221 using fasteners extending into LED mounting holes 234 of cooling plate 221. Light generator 220 may directly contact first face 235 of cooling plate 221. Cooling plate 221 may cool light generator 220 by transferring heat from light generator 220 through first face 235 to coolant 236. Coolant 236 may take the form of any desirable type of liquid. By having liquid coolant 236, cooling plate 221 may be smaller than an air cooling system. Coolant 236 may be present within cavity 237 formed by first face 235 and second face 238. Coolant 236 is provided to cooling plate 221 using coolant ports 239.

In some illustrative examples, at least one of cavity 237, first face 235, or second face 238 may have features selected to aid in heat transfer. For example, internal posts 240 may be present within cavity 237. Internal posts 240 may be formed or attached to at least one of first face 235 or second face 238. Internal posts 240 may create a greater surface area for transfer of heat to coolant 236. Internal posts 240 may also increase the turbulence of coolant 236 within cavity 237 which may increase the heat transfer of coolant 236. Internal posts 240 may include partial posts 241. Partial posts 241 may only extend a partial distance between first face 235 and second face 238 of cooling plate 221. Cooling plate 221 may further include mounting holes 242 for mounting cooling plate 221 to a structure.

Light housing 219 may house light generator 220. Light housing 219 may interface with cooling plate 221 to substantially surround light generator 220. Light housing 219 may include window 243, retainer 244, and housing 245. Window 243 may be formed of a material such that light 224 generated by light generator 220 may travel substantially unobstructed through window 243. Retainer 244 may hold window 243 within light housing 219. Retainer 244 may interface with housing 245. For example, retainer 244 has connector 246. Connector 246 may take the form of a number of threads, a quick release connector, a number of fasteners, or some other desirable form of connector. Connector 246 may interface with first connector 247 of housing 245.

First connector 247 may be one of number of connectors 248. Number of connectors 248 may take the form of threads 249, quick release 250, a number of fasteners, or some other desirable forms of connectors. First connector 247 may be positioned at first end 251 of housing 245. First end 251 of housing 245 may be associated with second end 252 of forming cup attachment 223. Second connector 253 of number of connectors 248 may be positioned at second end 254 of housing 245. Second end 254 of housing 245 may be associated with cooling plate 221. For example, second connector 253 may be used to connect housing 245 to cooling plate 221.

Light housing 219 may be used to protect light emitting diode array 233 of light generator 220 from contaminants, such as dust, or from other undesirable environmental conditions. As a result of window 243, light generator 220 may be protected from undesirable environmental conditions even if forming cup attachment 223 is removed from light housing 219.

Forming cup attachment 223 may be used to associate forming cup 222 with light generator 220. Forming cup attachment 223 may include gaskets 255, retainer 256, and housing 257. Second end 252 of housing 257 may be associated with light housing 219 using second connector 258 of number of connectors 259. Number of connectors 259 may take the form of threads 260, quick release 261, a number of fasteners, or other desirable forms of connectors.

First connector 262 of number of connectors 259 is positioned at first end 263 of housing 257. Retainer 256 of forming cup attachment 223 is associated with first end 263 of housing 257. For example, connector 264 may be associated with first connector 262. Connector 264 may take the form of a number of threads, a quick release connector, a number of fasteners, or some other desirable form of connector. Retainer 256 may retain forming cup 222 within sealing assembly 212.

Gaskets 255 may be placed on either side of base 265 of forming cup 222. As a result, a gasket of gaskets 255 may contact housing 257 and base 265 of forming cup 222. Another gasket of gaskets 255 may contact retainer 256 and base 265 of forming cup 222. Gaskets 255 may protect material 266 of forming cup 222 from damage. For example, gaskets 255 may protect base 265 from chipping against housing 257 or retainer 256 due to vibration or other movement of sealing assembly 212.

Forming cup 222 may include body 267 and base 265. Forming cup 222 may be formed of material 266 that is substantially transparent 268 to at least one wavelength of number of wavelengths 225 generated by light generator 220. In some illustrative examples, material 266 may be quartz or silica. Material 266 may be selected such that material 266 is substantially transparent to UV and visible wavelengths.

Body 267 may have length 270, angle 271, and internal cavity 272. Forming cup 222 may have a shape to direct light 224 to sealant 213 contained within internal cavity 272 of forming cup 222. In some illustrative examples, angle 271 is present across all of length 270. In some illustrative examples, angle 271 may only be present in a portion of body 267. The portion of body 267 having angle 271 may be referred to as angled portion 273. Angle 271 may be selected such that body 267 does not interfere with a neighboring structure. For example, angle 271 may be selected such that body 267 covers fastener 215 and does not contact the pre-existing cured sealant over other fasteners in number of fasteners 204.

Reflective coating 274 may be applied to the exterior of angled portion 273. Reflective coating 274 may be a material selected to reflect at least one of number of wavelengths of light 224. Reflective coating 274 may reflect at least a portion of light 224 so that minimal light is leaked to platform 201. Further, reflective coating 274 may reflect at least a portion of light 224 such that a greater intensity of light 224 reaches sealant 213.

Reflective coating 274 may take the form of any desirable type of material. Reflective coating 274 may be added to angled portion 273 in any desirable process. For example, reflective coating 274 may take the form of a film, a paint, a foil, or any other type of coating. Reflective coating 274 may be sprayed on, painted on, adhered on, or may be applied through any other desirable process.

Internal cavity 272 of body 267 has inner mold line 275. Inner mold line 275 may provide shape to sealant 213. As a result, inner mold line 275 is substantially complementary to outer mold line 276 of sealant 213.

To apply sealant 213 to fastener 215, sealant 213 in uncured form may be added to internal cavity 272. Forming cup 222 may be positioned relative to fastener 215 such that fastener 215 is positioned in internal cavity 272. With fastener 215 positioned in internal cavity 272, light generator 220 may generate light 224 to cure sealant 213. After curing sealant 213, forming cup 222 may be moved away from fastener 215 leaving sealant 213 over first end 214 of fastener 215. Internal cavity 272 may have release layer 277. Release layer 277 may increase the ease of separating sealant 213 from forming cup 222 after curing.

Internal cavity 272 may be configured to fit over first end 214 of fastener 215. Internal cavity 272 must be large enough to cover first end 214 of fastener 215. First end 214 may be shorter than some others of number of first ends 208. First end 214 may also be longer than some others of number of first ends 208.

In some illustrative examples, internal cavity 272 may cover all of number of first ends 208 including first end 214. In some illustrative examples, internal cavity 272 may not be designed to cover all of number of first ends 208. When internal cavity 272 is not designed to cover all of number of first ends 208, forming cup 222 may be removed from sealing assembly 212 and replaced with forming cup 278. In these illustrative examples, forming cup 222 and forming cup 278 may be interchangeable. Forming cup 278 may be stored with a number of other interchangeable forming cups for sealing assembly 212.

Forming cup 278 has base 279. Base 279 is substantially the same as base 265. By having base 279 and base 265 substantially the same, forming cup 222 and forming cup 278 may be easily interchangeable. When connector 264 is a quick release connector, forming cup 222 and forming cup 278 may be quickly and easily exchanged in sealing assembly 212.

Forming cup 278 has body 280. At least one aspect of body 280 is different than body 267. At least one of length 281, angle 282, or internal cavity 283 may be different than length 270, angle 271, or internal cavity 272 of body 267.

Angle 282 may be different from angle 271. Angle 282 may be different from angle 271 when forming cup 278 is used in areas in which number of fasteners 204 has a different spacing than an area in which forming cup 222 is used. For example, angle 282 may be steeper to fit between number of fasteners 204 with tighter spacing.

Internal cavity 283 may have inner mold line 284 and release layer 285. In some illustrative examples, inner mold line 284 may be different than inner mold line 275. Inner mold line 284 may be different than inner mold line 275 to create a cured sealant with a different shape. Inner mold line 284 may also accommodate a first end with a size that is different from first end 214.

Sealing assembly 212 may take the form of end effector 286. Sealing assembly 212 may have mount 287 to allow sealing assembly 212 to connect to robotic arm 288. In some illustrative examples, cooling plate 221 may be connected to mount 287 using mounting holes 242. Robotic arm 288 may move sealing assembly 212 within fuel tank system 202. Robotic arm 288 may move sealing assembly 212 from fastener to fastener in number of fasteners 204.

Robotic arm 288 may move sealing assembly 212 with sealant 213 to fastener 215. Sealing assembly 212 may apply light 224 to sealant 213 to cure sealant 213. Light 224 applied to sealant 213 may have number of characteristics 289. Number of characteristics 289 may be configured to cure sealant 213 on first end 214 of fastener 215. Number of characteristics 289 may include at least one of a wavelength of number of wavelengths 225, intensity, or duration. Number of characteristics 289 may be selected based on the selection of at least one of resin 227 or photoinitiator 226, or outer mold line 276. Number of characteristics 289 may be changed based on changing at least one of resin 227 or photoinitiator 226, or outer mold line 276.

The illustration of manufacturing environment 200 in FIGS. 2A and 2B is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

Figure 3:
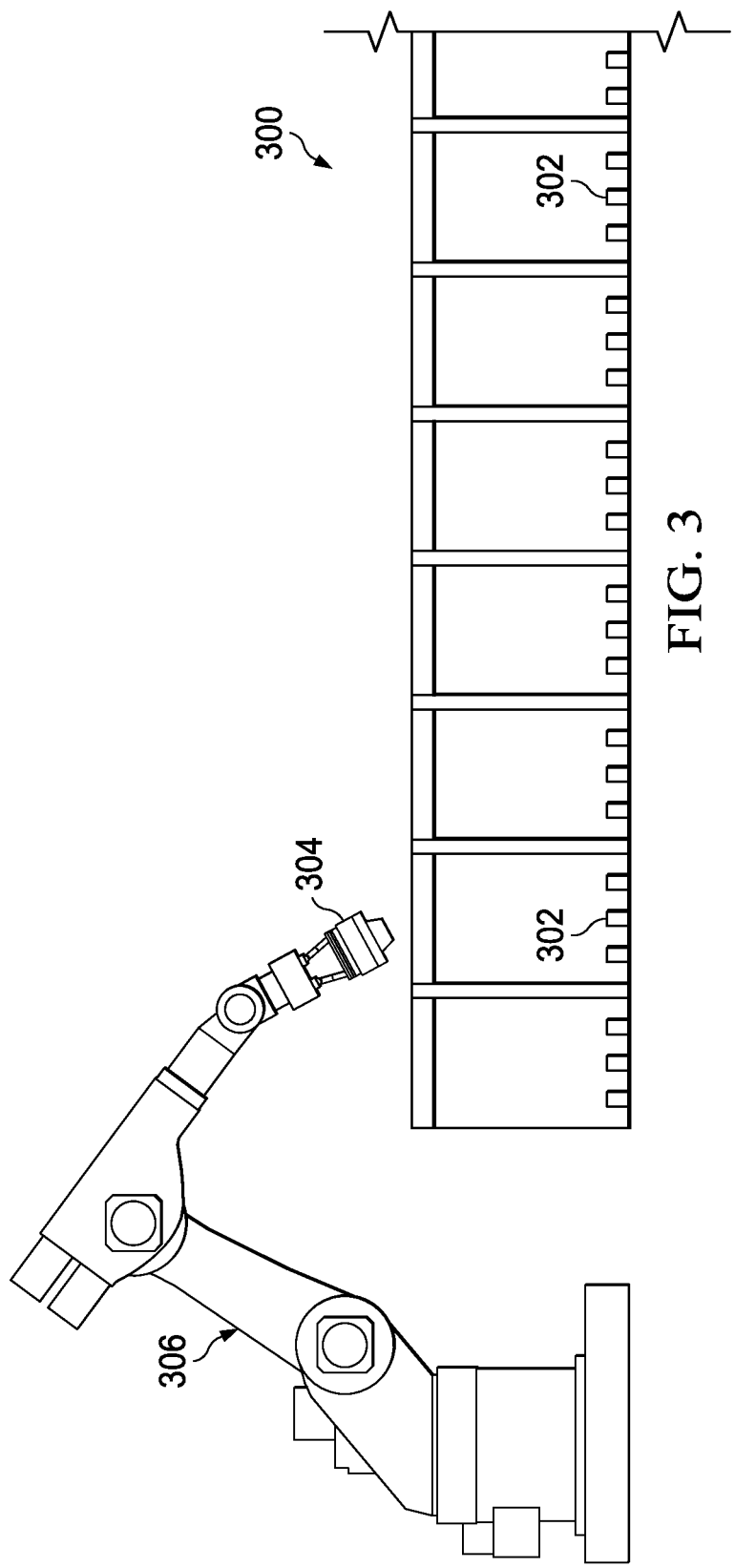
FIG. 3 is an illustration of a sealing assembly in a fuel tank in accordance with an illustrative embodiment.

Turning now to FIG. 3, an illustration of a sealing assembly in a fuel tank is depicted in accordance with an illustrative embodiment. Fuel tank 300 may be a physical implementation of fuel tank 205 shown in block form in FIGS. 2A and 2B. Fuel tank 300 may be an internal view of at least one of fuel tank 122 or fuel tank 124 in FIG. 1.

As depicted, fuel tank 300 has number of fasteners 302. Sealing assembly 304 may be moved within fuel tank 300 by robotic arm 306 to place and cure sealant over each of number of fasteners 302. Sealing assembly 304 may be a physical implementation of sealing assembly 212 of FIGS. 2A and 2B. Robotic arm 306 may be a physical implementation of robotic arm 288 of FIGS. 2A and 2B.

Figure 4:
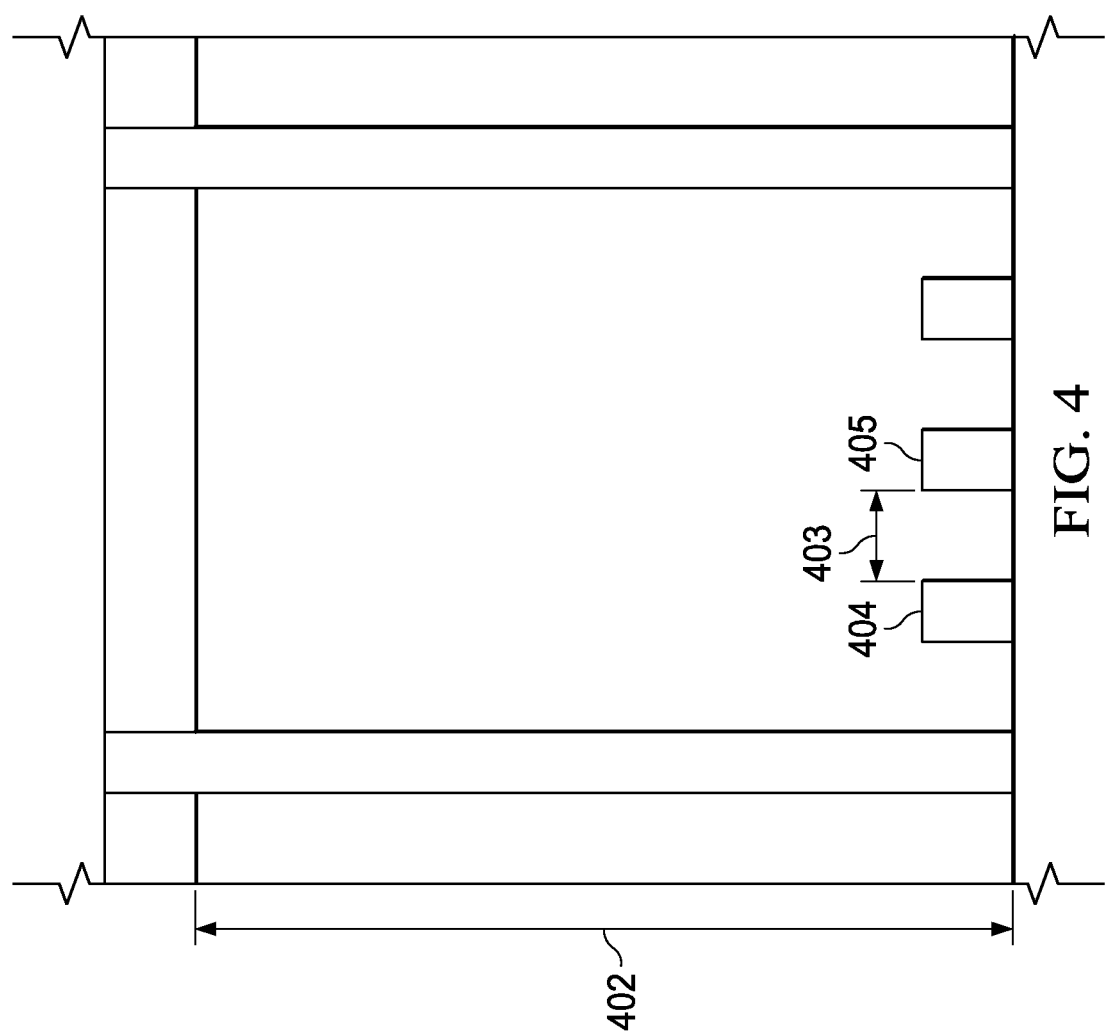
FIG. 4 is an illustration of a fuel tank in accordance with an illustrative embodiment.

Turning now to FIG. 4, an illustration of a fuel tank is depicted in accordance with an illustrative embodiment. View 400 may be a view of a portion of fuel tank 300. As depicted, height 402 of fuel tank 300 is limited. Further, distance 403 between fastener 404 and fastener 405 of number of fasteners 302 is relatively small. At least one of height 402 or distance 403 may increase the difficulty of applying sealant onto number of fasteners 302. As a result, any sealing assembly to be used in fuel tank 300 must be small enough to maneuver within fuel tank 300 and apply and cure sealant to each of number of fasteners 302.

Figure 5:
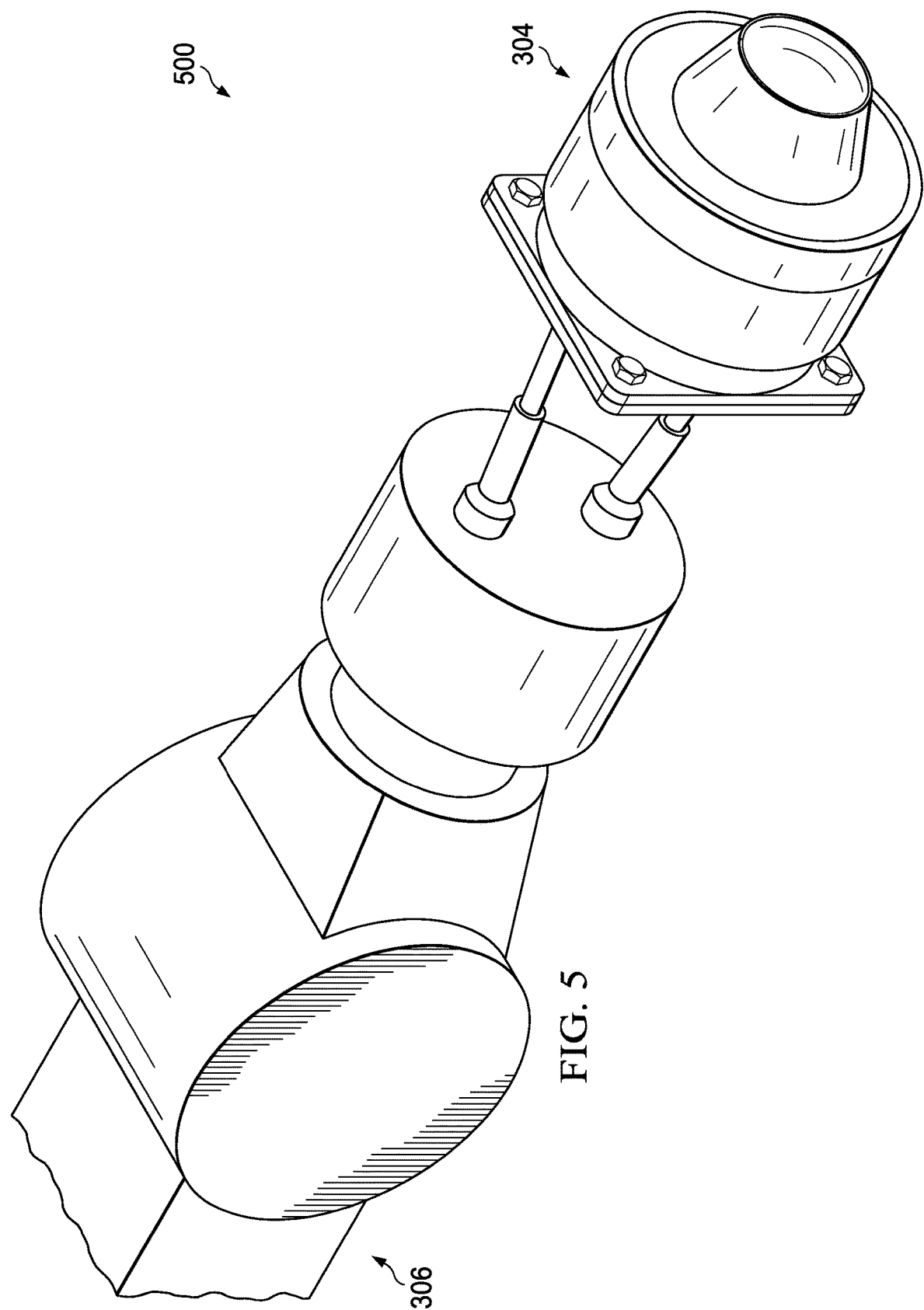
FIG. 5 is an illustration of a sealing assembly attached to a robotic arm in accordance with an illustrative embodiment.

Turning now to FIG. 5, an illustration of a sealing assembly attached to a robotic arm is depicted in accordance with an illustrative embodiment. View 500 may be a view of sealing assembly 304 and robotic arm 306 of FIG. 3 outside of fuel tank 300.

This illustration is non-limiting to the types of robotic arms or connections that may be used to maneuver sealing assembly 304. For example, although as depicted robotic arm 306 includes a movement system taking the form of two actuators, any type of movement system may be used to maneuver sealing assembly 304. Further, a movement system may maneuver sealing assembly 304 in any desirable number of degrees of freedom. For example, a movement system may include any desirable number of actuators, any desirable number of joints, any desirable types of actuators, or any desirable types of joints. For example, a robotic arm or connection may include at least one of a rotary joint, a twisting joint, a co-linear joint, a spherical joint, an orthogonal joint, a revolving joint, or any other desirable type of joint. In one illustrative example, the movement system may include a hexapod movement system such as a stewart platform.

Figure 6:
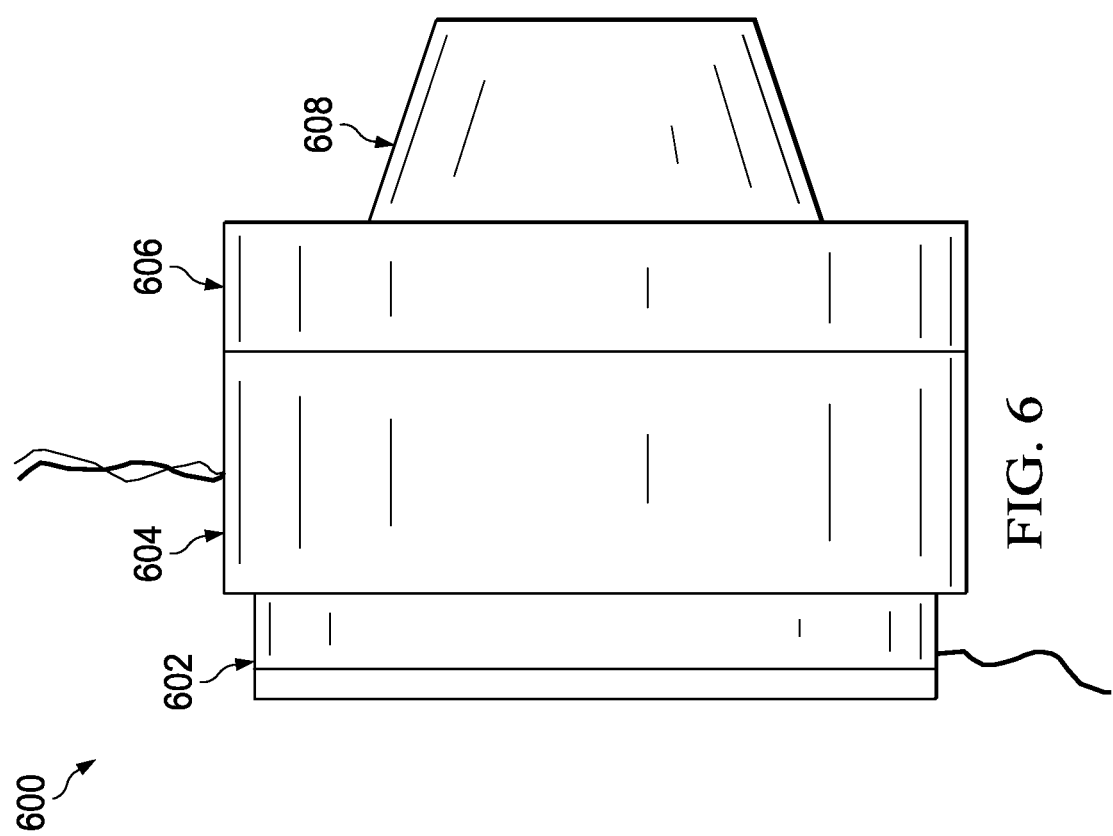
FIG. 6 is an illustration of a side view of a sealing assembly in accordance with an illustrative embodiment.

Turning now to FIG. 6, an illustration of a side view of a sealing assembly is depicted in accordance with an illustrative embodiment. Sealing assembly 600 may be a physical implementation of sealing assembly 212 shown in block form in FIGS. 2A and 2B. In some illustrative examples, sealing assembly 600 may be the same as sealing assembly 304 of FIG. 3. Sealing assembly 600 has cooling plate 602, light housing 604, forming cup attachment 606, and forming cup 608.

Figure 7:
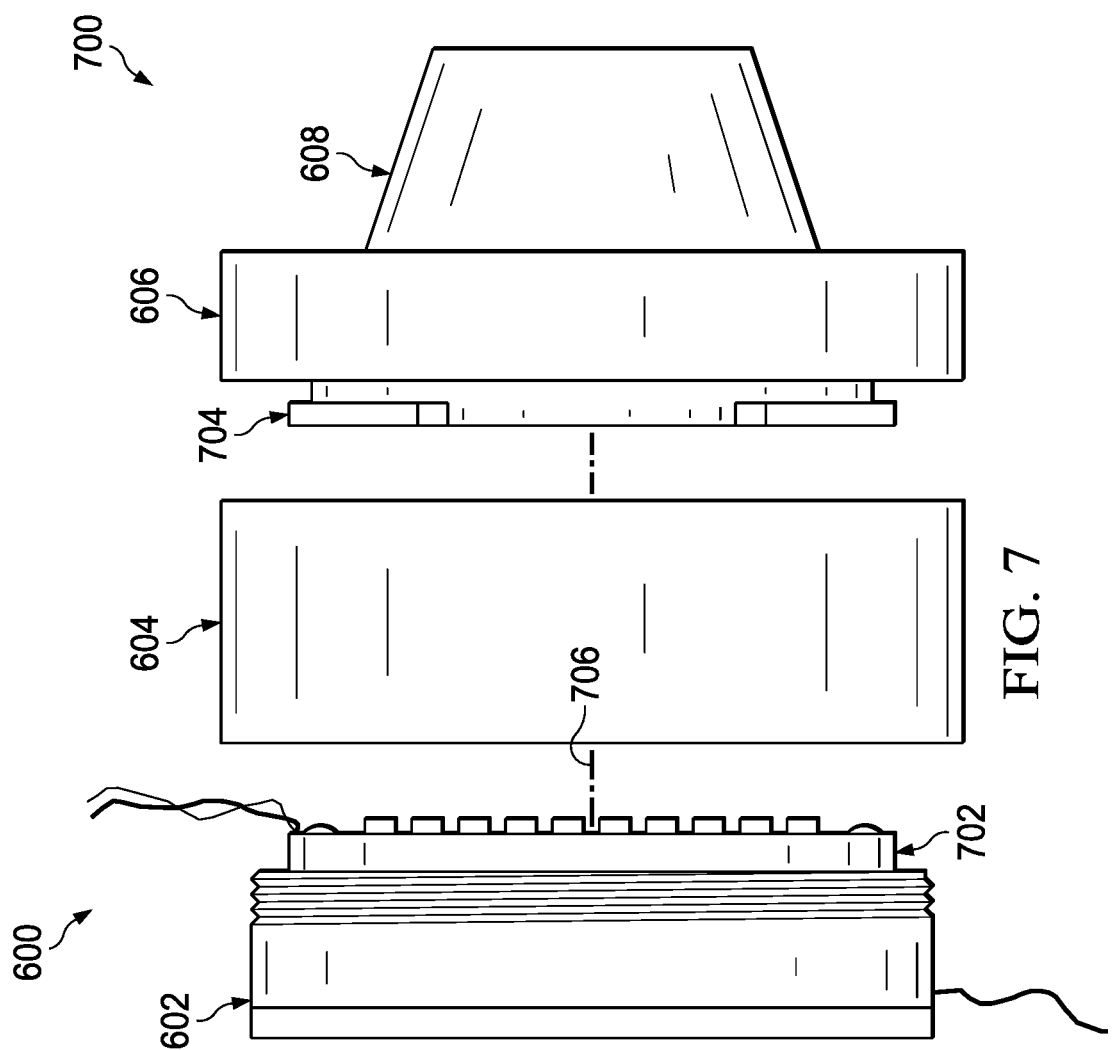
FIG. 7 is an illustration of a partially exploded side view of a sealing assembly in accordance with an illustrative embodiment.

Turning now to FIG. 7, an illustration of a partially exploded side view of a sealing assembly is depicted in accordance with an illustrative embodiment. View 700 is an exploded view of sealing assembly 600. As depicted, light generator 702 is associated with cooling plate 602. When assembled, light housing 604 encompasses light generator 702, protecting light generator 702 from contaminants and other undesirable environmental features.

Further, view 700 also exposes second connector 704 of forming cup attachment 606 for connection to light housing 604. Second connector 704 may be a quick release connector. Forming cup attachment 606, second connector 704, and light housing 604 illustrate an embodiment of forming cup attachment 223, second connector 258, and light housing 219 presented in the block diagram of FIG. 2A. When assembled together, all components in FIG. 7 have a common central axis 706.

Figure 8:
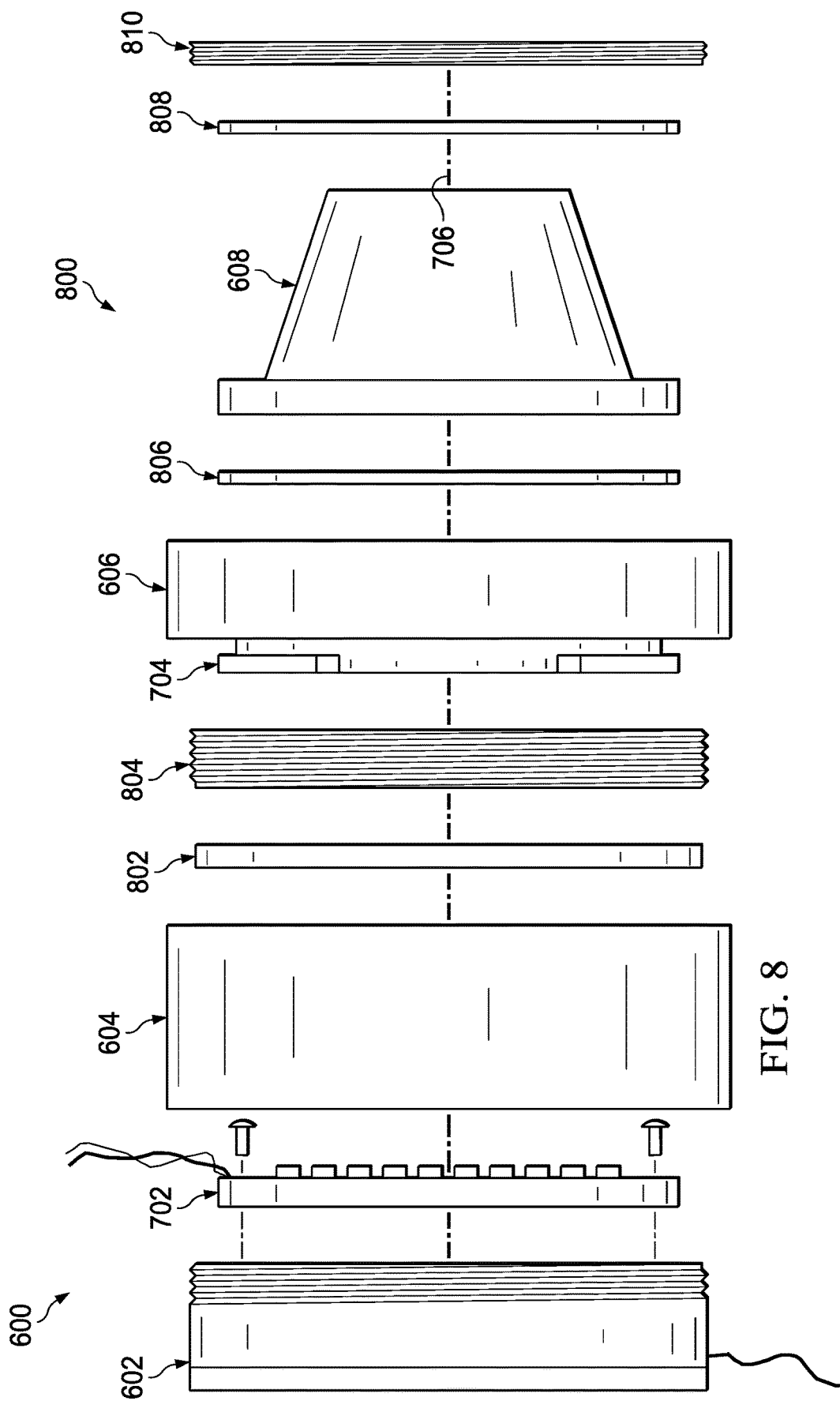
FIG. 8 is an illustration of a fully exploded side view of a sealing assembly in accordance with an illustrative embodiment.

Turning now to FIG. 8, an illustration of a fully exploded side view of a sealing assembly is depicted in accordance with an illustrative embodiment. View 800 is a completely exploded view of sealing assembly 600. In view 800, window 802 and retainer 804 of light housing 604 are shown. Retainer 804 may hold window 802 in place within light housing 604. In view 800, gasket 806, gasket 808, and retainer 810 are shown. Gasket 806 and gasket 808 may prevent or reduce damage to forming cup 608 when sealing assembly 600 is assembled. Retainer 810 may hold gasket 806, gasket 808, and forming cup 608 within forming cup attachment 606. When assembled together, all components in FIG. 8 have a common central axis 706.

Figure 9:
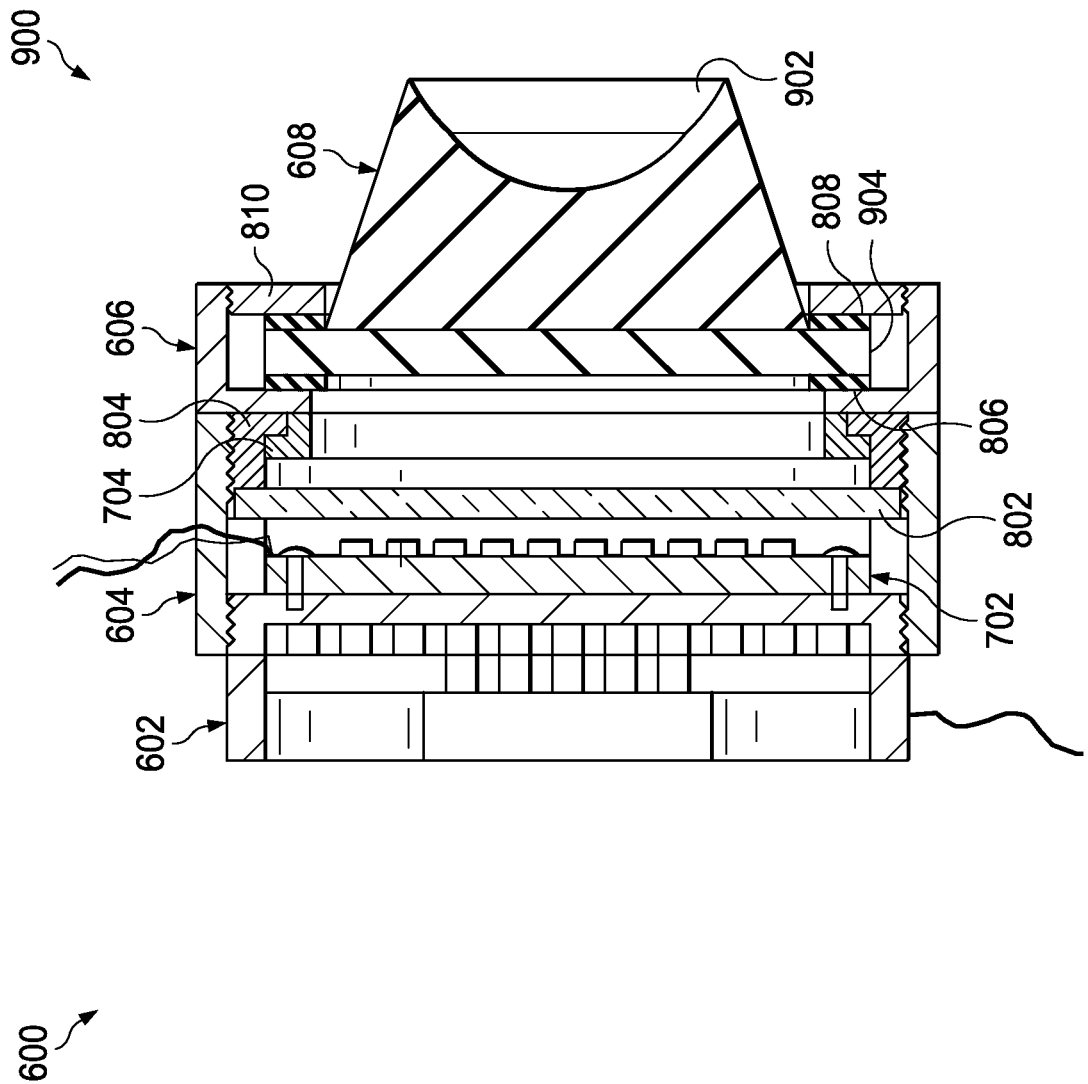
FIG. 9 is an illustration of a cross-sectional side view of a sealing assembly in accordance with an illustrative embodiment.

Turning now to FIG. 9, an illustration of a cross-sectional side view of a sealing assembly is depicted in accordance with an illustrative embodiment. View 900 is a cross-sectional view of sealing assembly 600. In view 900, internal cavity 902 of forming cup 608 is shown. Further, in view 900, gasket 806 and gasket 808 contact base 904 of forming cup 608.

Figure 10:
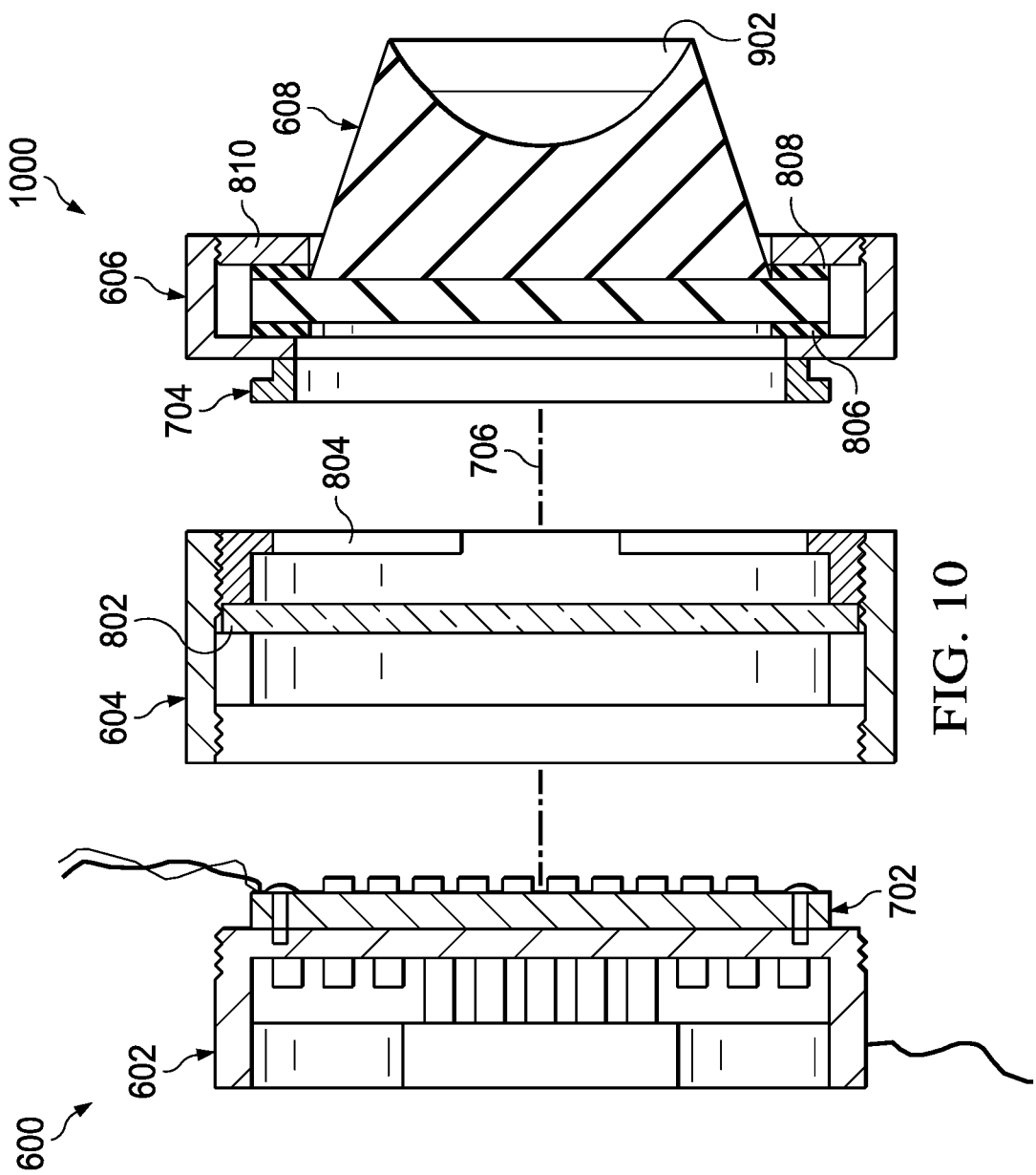
FIG. 10 is an illustration of a cross-sectional partially exploded side view of a sealing assembly in accordance with an illustrative embodiment.

Turning now to FIG. 10, an illustration of a cross-sectional partially exploded side view of a sealing assembly is depicted in accordance with an illustrative embodiment. View 1000 may be a cross-sectional view of view 700 in this figure. When assembled together, all components in FIG. 10 have a common central axis 706.

Figure 11:
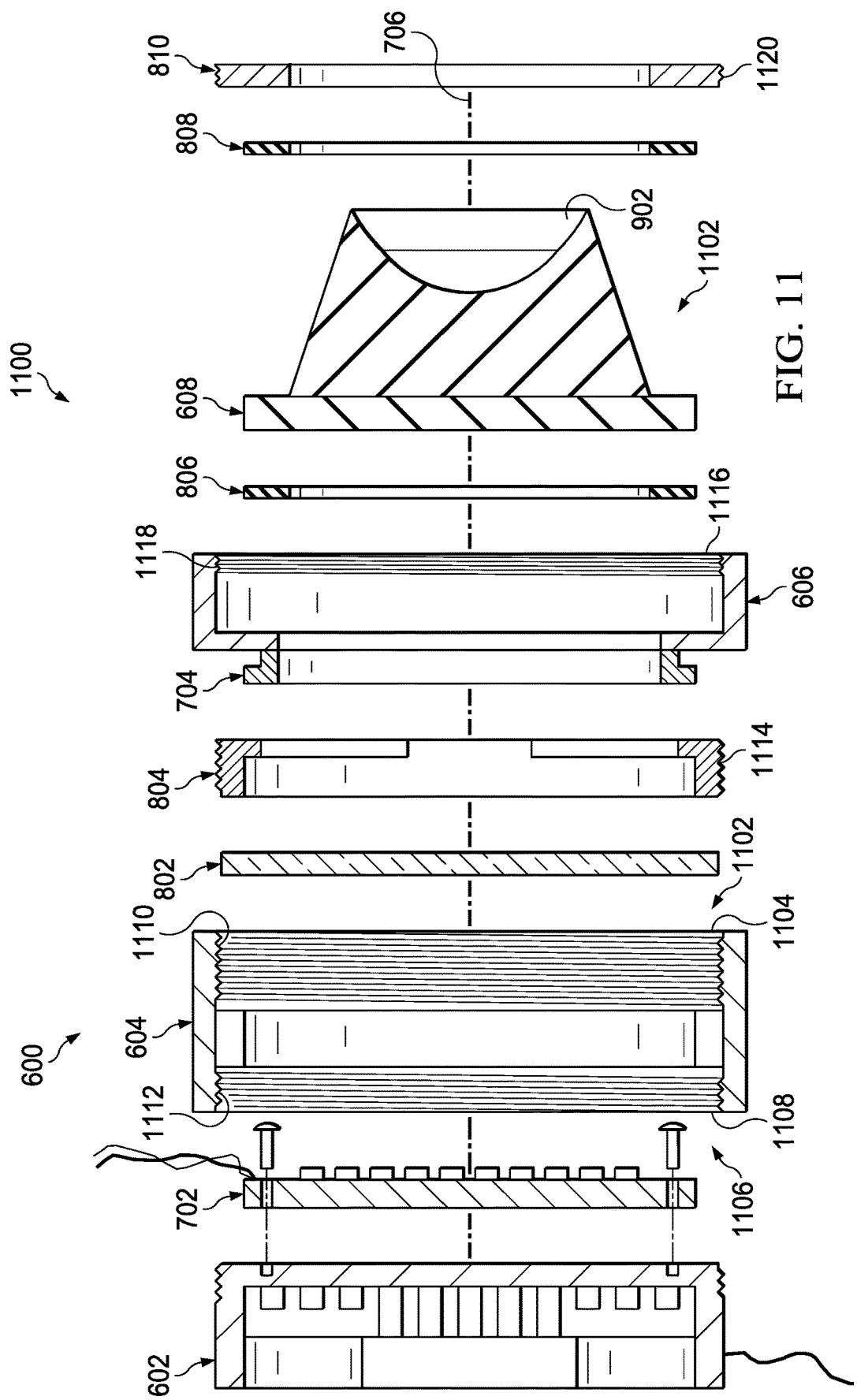
FIG. 11 is an illustration of a cross-sectional fully exploded side view of a sealing assembly in accordance with an illustrative embodiment.

Turning now to FIG. 11, an illustration of a cross-sectional fully exploded side view of a sealing assembly is depicted in accordance with an illustrative embodiment. View 1100 may be a cross-sectional view of view 800 in this figure.

As can be seen in view 1100, light housing 604 has first end 1102 with connector 1104 and second end 1106 with connector 1108. As depicted, connector 1104 is formed of threads 1110 and connector 1108 is formed of threads 1112. Threads 1112 may interface with cooling plate 602 to encompass light generator 702. Threads 1114 of retainer 804 may interface with threads 1112 to hold window 802 in place within light housing 604. Connector 1116 of forming cup attachment 606 may take the form of threads 1118. As illustrated, threads 1120 of retainer 810 may interface with threads 1118 to hold forming cup 608 in place.

In some illustrative examples, some of the connectors may take the form of a connector other than threads. For example, at least one of threads 1118 or threads 1120 may take the form of a bayonet connector or other form of quick release connector. By retainer 810 having a quick release connector, forming cup 608 may be quickly exchanged for a different forming cup. When assembled together, all components in FIG. 11 have a common central axis 706.

Turning now to FIG. 12, an illustration of a side cross-sectional view of a forming cup is depicted in accordance with an illustrative embodiment. Forming cup 1200 may be a physical implementation of forming cup 222 of FIGS. 2A and 2B. Forming cup 1200 may be a depiction of forming cup 608 of FIG. 6.

Forming cup 1200 has base 1202 and body 1204. Body 1204 has angled portion 1206 and internal cavity 1208. Angled portion 1206 has angle 1210. Angle 1210 may be configured such that body 1204 may fit between two fasteners such as number of fasteners 302 of FIG. 3. Angle 1210 may further be configured such that body 1204 may fit between two fasteners with sealant applied and cured.

Body 1204 also has height 1212. Height 1212 may be configured such that base 1202 does not undesirably contact a structure. For example, height 1212 may be configured such that base 1202 does not contact the number of fasteners.

Forming cup 1200 may have reflective coating 1214 on the exterior of angled portion 1206 such that light 1216 reflects towards internal cavity 1208. Reflective coating 1214 may be selected to substantially reflect specific wavelengths of light. For example, reflective coating 1214 may be selected to substantially reflect at least one wavelength generated by a light generator such as light generator 220 of FIGS. 2A and 2B.

Release layer 1218 may be present on the surface of internal cavity 1208. Release layer 1218 may ease the release of a sealant after curing.

Turning now to FIG. 13, an illustration of a side cross-sectional view of a forming cup is depicted in accordance with an illustrative embodiment. Forming cup 1300 may be a physical implementation of forming cup 278 of FIGS. 2A and 2B. Forming cup 1300 may be a depiction of a replacement forming cup for forming cup 608 of FIG. 6.

Forming cup 1300 has base 1302 and body 1304. Base 1302 may be substantially the same as base 1202 of FIG. 12. For example, base 1302 may have substantially similar dimensions as base 1202 of FIG. 12. As a result, forming cup 1300 may be interchangeable with forming cup 1200.

Body 1304 has angled portion 1306 and internal cavity 1308. Angled portion 1306 has angle 1310. Angle 1310 may be configured such that body 1304 may fit between two fasteners such as number of fasteners 302 of FIG. 3. Angle 1310 may further be configured such that body 1304 may fit between two fasteners with sealant applied and cured.

Body 1304 also has height 1312. Height 1312 may be configured such that base 1302 does not undesirably contact a structure. For example, height 1312 may be configured such that base 1302 does not contact the number of fasteners.

Forming cup 1300 may have reflective coating 1314 on the exterior of angled portion 1306 such that light reflects towards internal cavity 1308. Reflective coating 1314 may be selected to substantially reflect specific wavelengths of light. For example, reflective coating 1314 may be selected to substantially reflect at least one wavelength generated by a light generator such as light generator 220 of FIGS. 2A and 2B.

Release layer 1316 may be present on the surface of internal cavity 1308. Release layer 1316 may ease the release of a sealant after curing. As depicted, internal cavity 1308 is different than internal cavity 1208 of FIG. 12. Internal cavity 1308 has a different shape than internal cavity 1208 of FIG. 12. Internal cavity 1308 is deeper than internal cavity 1208 of FIG. 12.

As a result, internal cavity 1308 may cover a longer first end of a fastener than internal cavity 1208 may cover. Further, in some examples, during curing of a sealant, internal cavity 1308 may have more sealant within internal cavity 1308 than may be contained within internal cavity 1208.

Forming cup 1300 may be an interchangeable forming cup. Forming cup 1300 may be added or removed from a sealing assembly. Forming cup 1300 may be exchanged for forming cup 1200 or other interchangeable forming cups.

Figure 14:
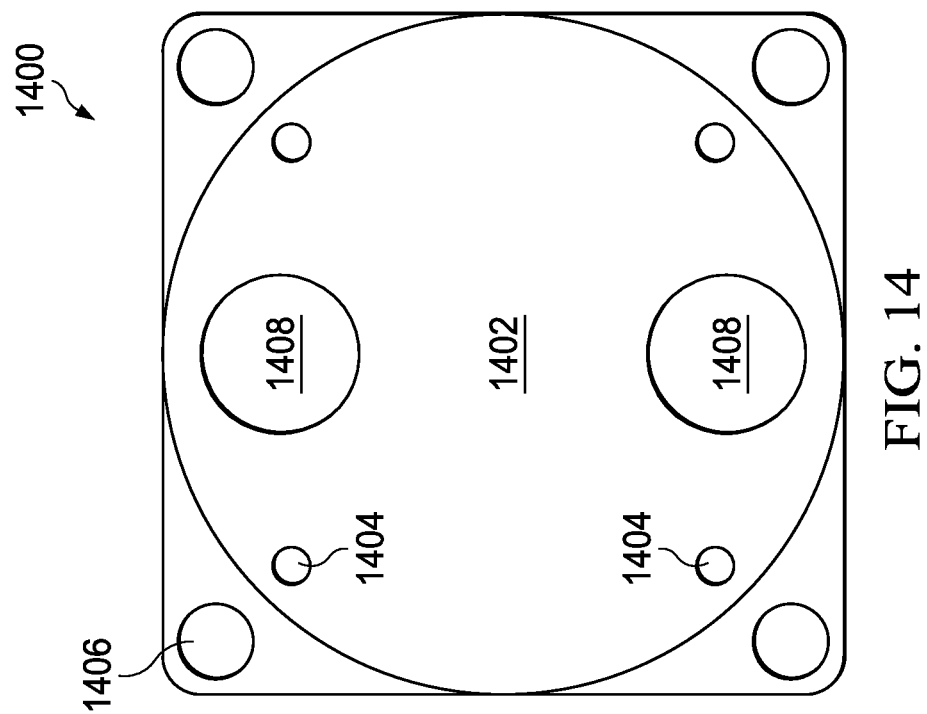
FIG. 14 is an illustration of a back view of a cooling plate in accordance with an illustrative embodiment.

Turning now to FIG. 14, an illustration of a back view of a cooling plate is depicted in accordance with an illustrative embodiment. Cooling plate 1400 may be a physical implementation of cooling plate 221 shown in block form in FIGS. 2A and 2B. Cooling plate 1400 has second face 1402, LED mounting holes 1404, mounting holes 1406, and coolant ports 1408. Coolant ports 1408 extend through second face 1402. Coolant may flow through coolant ports 1408 and enter a cavity (not depicted).

Mounting holes 1406 may be used to mount cooling plate 1400 to a structure. For example, mounting holes 1406 may be used to mount cooling plate 1400 to a mount to form an end effector. The mount may be used to attach cooling plate 1400 to a robotic arm.

Figure 15:
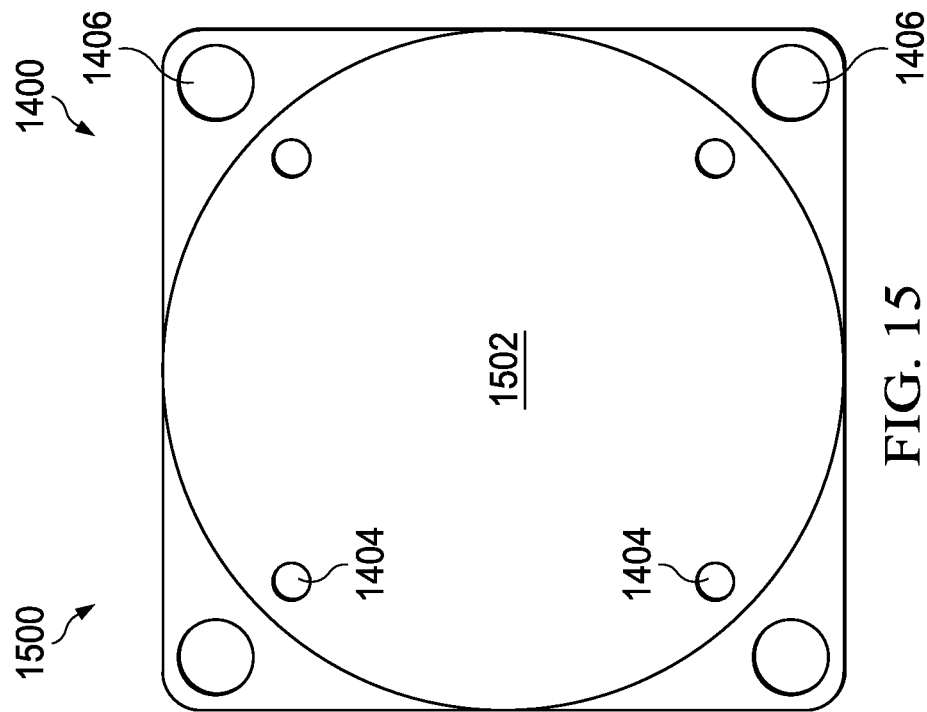
FIG. 15 is an illustration of a front view of a cooling plate in accordance with an illustrative embodiment.

Turning now to FIG. 15, an illustration of a front view of a cooling plate is depicted in accordance with an illustrative embodiment. View 1500 may be a view of the front of cooling plate 1400. First face 1502 of cooling plate 1400 is visible in view 1500. First face 1502 may be configured to contact a lighting generator such as light generator 220 of FIGS. 2A and 2B. First face 1502 may be configured to transfer heat from a lighting generator to coolant within cooling plate 1400.

Figure 16:
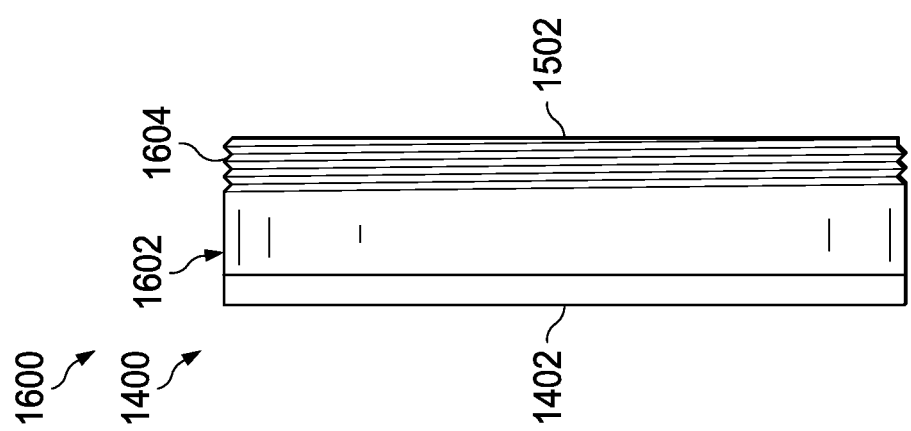
FIG. 16 is an illustration of a side view of a cooling plate in accordance with an illustrative embodiment.

Turning now to FIG. 16, an illustration of a side view of a cooling plate is depicted in accordance with an illustrative embodiment. View 1600 may be a side view of cooling plate 1400. As can be seen in view 1600, cooling plate 1400 has connector 1602. A housing such as light housing 219 of FIGS. 2A and 2B may be associated with cooling plate 1400 using connector 1602. As depicted, connector 1602 may take the form of threads 1604. However, in other illustrative examples, connector 1602 may take the form of other desirable types of connectors.

Figure 17:
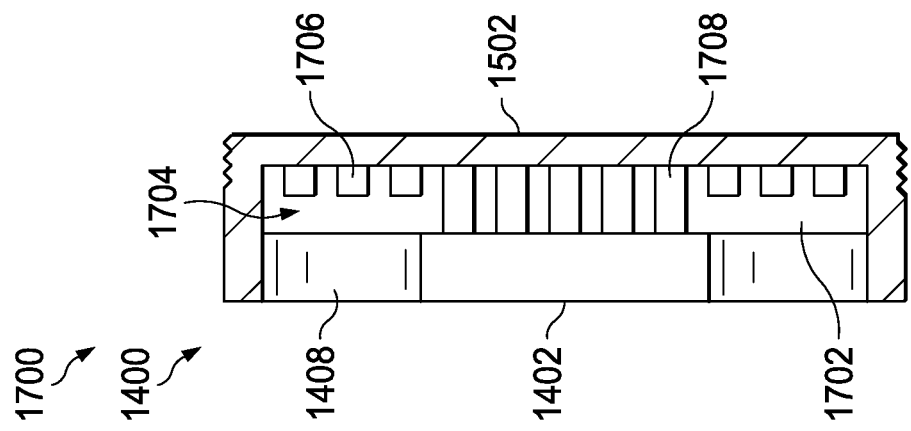
FIG. 17 is an illustration of a cross-sectional side view of a cooling plate in accordance with an illustrative embodiment.

Turning now to FIG. 17, an illustration of a cross-sectional side view of a cooling plate is depicted in accordance with an illustrative embodiment. View 1700 may be a cross-sectional view of cooling plate 1400. As can be seen in view 1700, cooling plate 1400 has cavity 1702. Coolant may flow into and out of cavity 1702 through coolant ports 1408. Plurality of posts 1704 is present within cavity 1702. Plurality of posts 1704 includes partial posts 1706 and full posts 1708. Full posts 1708 may extend the full thickness of cavity 1702. Partial posts 1706 may only extend into cavity 1702 a portion of the thickness of cavity 1702. Plurality of posts 1704 may increase heat transfer between first face 1502 and the coolant in cavity 1702.

Figure 18:
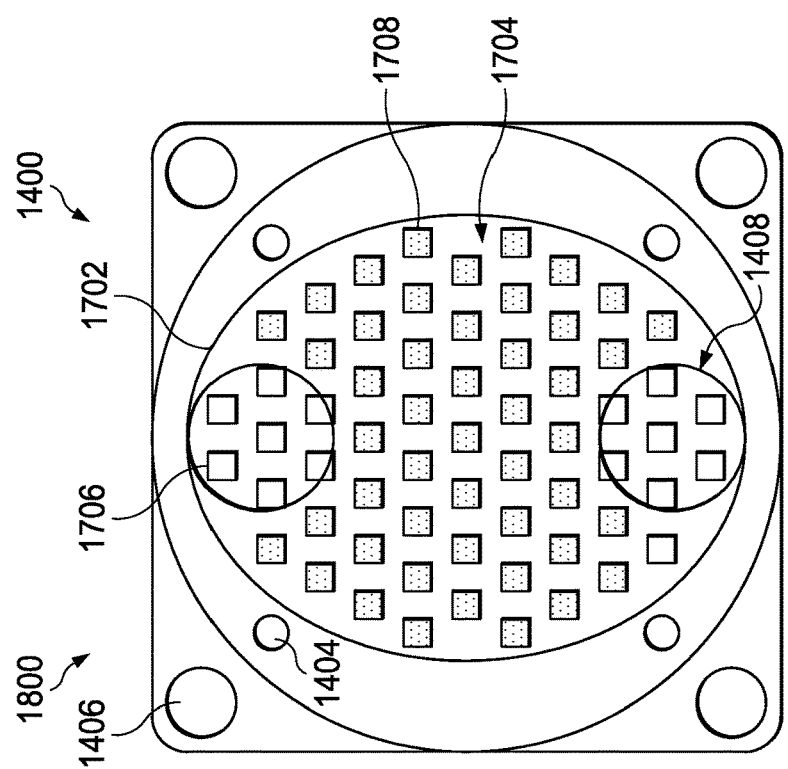
FIG. 18 is an illustration of a back view of a cooling plate with surfaces shown as transparent for demonstration purposes in accordance with an illustrative embodiment.

Turning now to FIG. 18, an illustration of a back view of a cooling plate with surfaces shown as transparent for demonstration purposes is depicted in accordance with an illustrative embodiment. View 1800 may be a back view of cooling plate in which second face 1402 is transparent.

Figure 19:
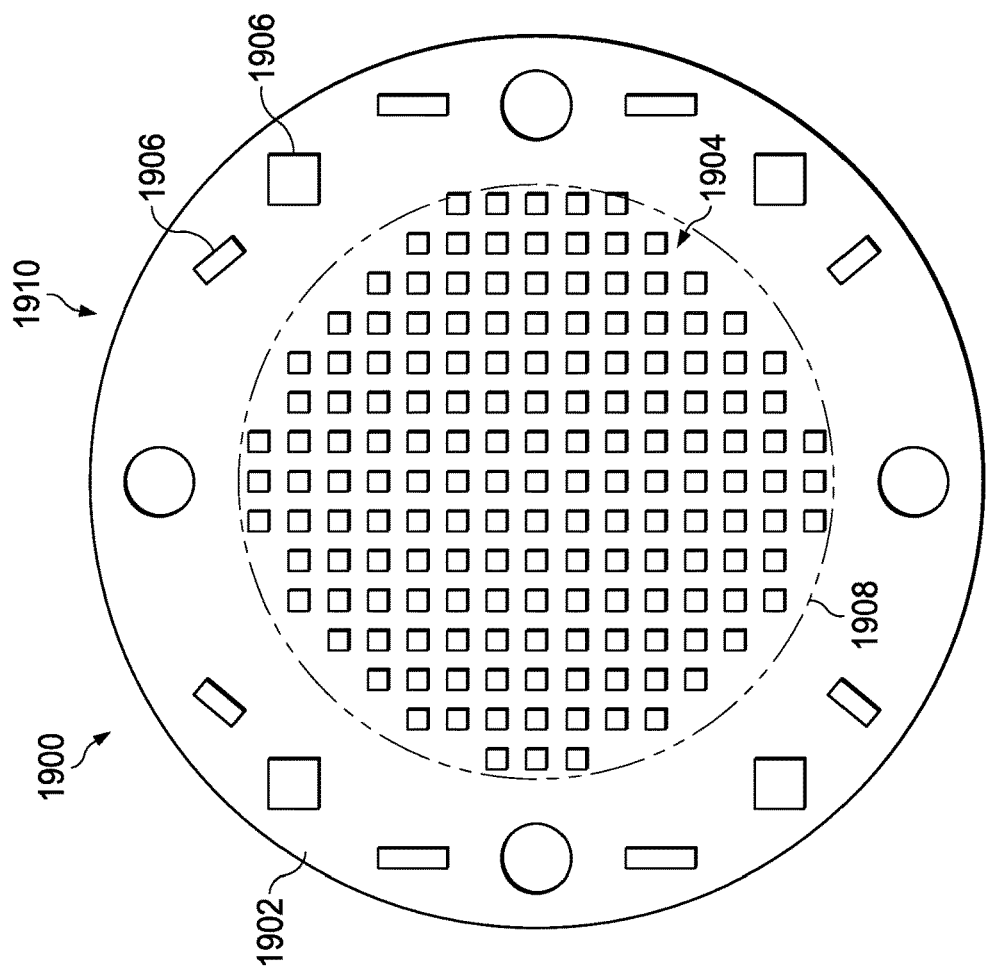
FIG. 19 is an illustration of a front view of a light generator in accordance with an illustrative embodiment.

Turning now to FIG. 19, an illustration of a front view of a light generator is depicted in accordance with an illustrative embodiment. Light generator 1900 may be a physical implementation of light generator 220 of FIGS. 2A and 2B. Light generator 1900 includes board 1902, light emitting diode array 1904, and support structures 1906. Light emitting diode array 1904 forms emissive region 1908. Emissive region 1908 may be the region that emits light. Emissive region 1908 may be designed based on a desired size or shape for a sealant to be cured. Emissive region 1908 may be configured based on the packing of light emitting diode array 1904. Light emitting diode array 1904 may have a desired density of packing. By increasing the density of packing, the light emitted by light emitting diode array 1904 may be increased.

Support structures 1906 are positioned at periphery 1910 of board 1902. Support structures 1906 may provide support to light emitting diode array 1904. For example, support structures 1906 may supply at least one of commands, electricity, signals, or other types of support to light emitting diode array 1904. Commands may be provided by a computer system to support structures 1906. Utilities may be provided to support structures 1906 by utility providers. The communication between at least one of a computer system or utilities and support structures 1906 may be facilitated through a communications medium such as at least one of a wired cable, an optical fiber, a wireless communications link, or other suitable types of media.

The different components shown in FIGS. 1 and 3-19 may be combined with components in FIGS. 2A and 2B, used with components in FIGS. 2A and 2B, or a combination of the two. Additionally, some of the components in FIGS. 1 and 3-19 may be illustrative examples of how components shown in block form in FIGS. 2A and 2B can be implemented as physical structures.

Figure 20:
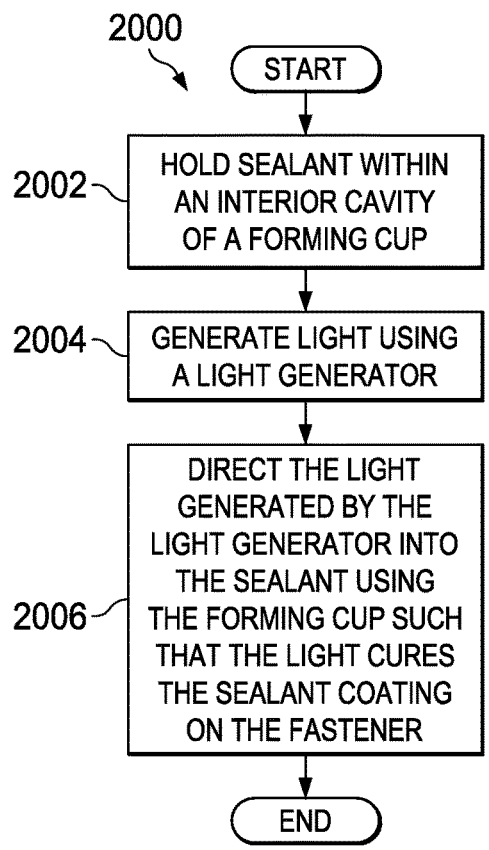
FIG. 20 is an illustration of a flowchart of a method for applying and curing a sealant coating on a fastener in accordance with an illustrative embodiment.

Turning now to FIG. 20, an illustration of a flowchart of a method for applying and curing a sealant coating on a fastener is depicted in accordance with an illustrative embodiment. Process 2000 may hold sealant within an interior cavity of a forming cup (operation 2002). Process 2000 may generate light using a light generator (operation 2004). Process 2000 may direct the light generated by the light generator into the sealant using the forming cup such that the light cures the sealant coating on the fastener (operation 2006). In some illustrative examples, generating the light using the light generator is performed until the sealant is cured to a desired extent.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the Figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram. Further, some blocks may not be implemented.

For example, process 2000 may also comprise moving the forming cup and sealant towards the fastener and moving the forming cup away from the sealant coating on the fastener after the sealant coating has been cured to a desired extent. In another illustrative example, the forming cup is a first forming cup. In this illustrative example, process 2000 may also comprise removing the first forming cup and installing a second forming cup relative to the light generator.

Figure 21:
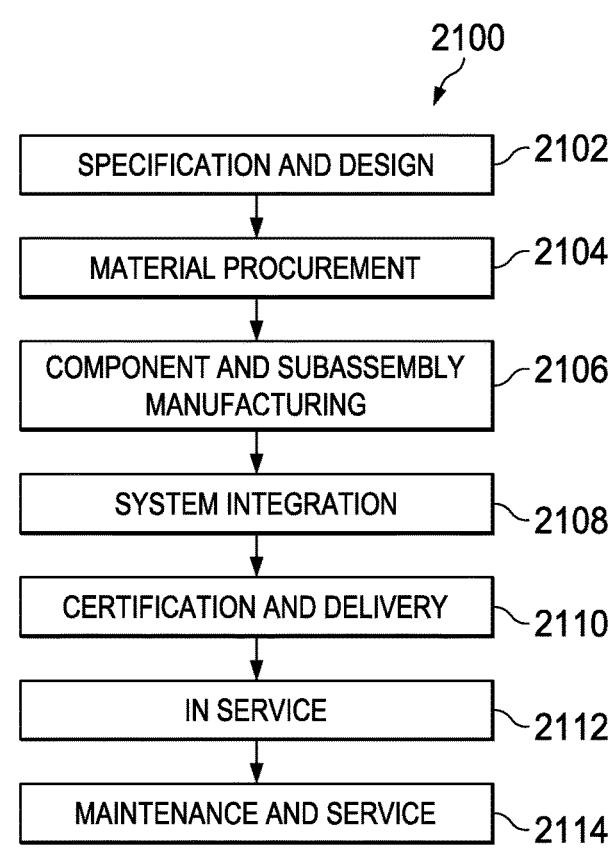
FIG. 21 is an illustration of an aircraft manufacturing and service method in the form of a block diagram in accordance with an illustrative embodiment.
Figure 22:
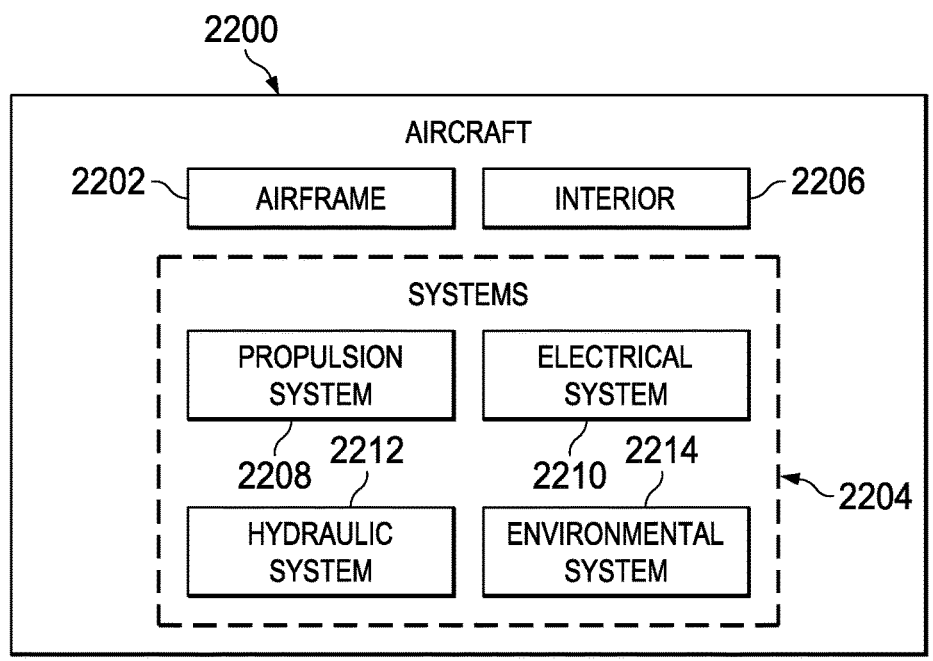
FIG. 22 is an illustration of an aircraft in the form of a block diagram in which an illustrative embodiment may be implemented.

The illustrative embodiments of the disclosure may be described in the context of aircraft manufacturing and service method 2100 as shown in FIG. 21 and aircraft 2200 as shown in FIG. 22. Turning first to FIG. 21, an illustration of a block diagram of an aircraft manufacturing and service method is depicted in accordance with an illustrative embodiment. During pre-production, aircraft manufacturing and service method 2100 may include specification and design 2102 of aircraft 2200 in FIG. 22 and material procurement 2104.

During production, component and subassembly manufacturing 2106 and system integration 2108 of aircraft 2200 in FIG. 22 takes place. Thereafter, aircraft 2200 in FIG. 22 may go through certification and delivery 2110 in order to be placed in service 2112. While in service 2112 by a customer, aircraft 2200 in FIG. 22 is scheduled for routine maintenance and service 2114, which may include modification, reconfiguration, refurbishment, and other maintenance or service.

Each of the processes of aircraft manufacturing and service method 2100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 22, an illustration of a block diagram of an aircraft is depicted in which an illustrative embodiment may be implemented. In this example, aircraft 2200 is produced by aircraft manufacturing and service method 2100 in FIG. 21 and may include airframe 2202 with a plurality of systems 2204 and interior 2206. Examples of systems 2204 include one or more of propulsion system 2208, electrical system 2210, hydraulic system 2212, and environmental system 2214. Any number of other systems may be included. Although an aerospace example is shown, different illustrative embodiments may be applied to other industries, such as the automotive industry.

The method and apparatus embodied herein may be employed during at least one of the stages of aircraft manufacturing and service method 2100 in FIG. 21. One or more illustrative embodiments may be used during component and subassembly manufacturing 2106. For example, sealing assembly 212 may be used to apply and cure sealant on a number of fasteners during component and subassembly manufacturing 2106. Further, sealing assembly 212 may also be used to apply and cure sealant to fasteners during maintenance and service 2114.

The method and apparatus presented may reduce the amount of time needed to manufacture a fuel tank system. A sealant may be applied and cured over an end of a fastener using an end effector on a robotic arm. By using an end effector, the sealant may be applied and cured in less time than manually applying conventional seal caps. Manually applying conventional seal caps may take up to twenty minutes each. The time required to apply a conventional seal cap may be related to at least one of the location within the fuel tank system, the size of the end to be covered, the desired surface treatments, or other factors.

By using a sealing assembly to apply sealant, the application and curing processes may be reduced to less than a minute for each fastener. Thus, application time for the sealant may be reduced. By reducing sealant application time, manufacturing time of the fuel tank system may be reduced. By reducing sealant application time, manufacturing time of the fuel tank system may be reduced by hundreds of hours. In some illustrative examples, manufacturing time of the fuel tank system may be reduced by more than 1000 hours.

Still further, by using an end effector to apply and cure sealant, seal caps may not need to be inspected. By eliminating these inspections, manufacturing time may be further reduced.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A sealing assembly configured to form a sealant coating on a fastener, such that the sealing assembly comprises each of the following components having a common central axis:
   a light generator at an end of the sealing assembly connected to a cooling plate configured to connect to a robotic arm and configured to generate a light that comprises a number of characteristics that cures the sealant coating on the fastener;

a light housing configured to:

surround the light generator;

receive, at a first end of the light housing, a retainer of the light housing, said retainer configured to receive a first quick release connector;

a second end of the light housing configured to interface with the cooling plate to encompass the light generator;

a forming cup that comprises:

a base and a body;

a material substantially transparent to the light generated by the light generator; and a shape configured to direct the light to the sealant coating contained within an internal cavity of the forming cup; and a forming cup attachment located between the forming cup and the light housing; said forming cup attachment comprises the first quick release connector configured to removably connect to the light housing; and said forming cup attachment configured to retain the forming cup at a constant distance from the light generator within the sealing assembly, a retainer of the forming attachment.

2. The sealing assembly of claim 1 further comprising: the cooling plate connected to a liquid coolant supply system.

3. The sealing assembly of claim 1, wherein the forming cup further comprises at least one of a release layer positioned within the internal cavity, or a reflective coating associated with an angled portion of the forming cup.

4. The sealing assembly of claim 1, wherein the light generator comprises:

a light emitting diode array.

5. The sealing assembly of claim 4, wherein the light emitting diode array has a desired density of packing.

6. The sealing assembly of claim 5, wherein the light generator further comprises:

support structures around a periphery of the light emitting diode array, wherein the support structures control the light emitted by the light emitting diode array.

7. A method for applying and curing a sealant coating on a fastener using a sealing assembly for forming the sealant coating, the method comprising:

holding a sealant within an internal cavity of a forming cup of the sealing assembly, wherein the forming cup comprises :

a base and a body;

a number of characteristics for curing the sealant coating on the fastener;

a material substantially transparent to a light coming from a light generator at an end of the sealing assembly connected to a cooling plate configured to connect to a robotic arm; and a shape directing a light to the sealant coating within the internal cavity of the forming cup, the light comprising a number of characteristics for curing the sealant coating on the fastener and, such that the sealing assembly comprises:

a light housing surrounding the light generator and configured to:

receive, at a first end of the light housing, a retainer of the light housing configured to receive a first quick release connector;

receive, at a second end of the light housing, the cooling plate; wherein said light housing and the cooling plate encompass the light generator; and a forming cup attachment:

located between the forming cup and the light housing, said forming cup attachment comprising: the first quick release connector configured to removably connect to the light housing and retain a portion of the forming cup within the forming cup attachment and retain the forming cup a constant distance from the light generator within the sealing assembly; and a retainer of the forming cup attachment including threads configured to receive a second quick release connector configured to connect the forming cup to the forming cup attachment;

the robotic arm moving the forming cup over the fastener; and directing the light onto and curing the sealant coating.

8. The method of claim 7 further comprising: moving the sealing assembly including the light generator and the forming cup holding the sealant towards the fastener; and moving the sealing assembly including the light generator and the forming cup away from the sealant coating on the fastener after the sealant coating has been cured to a desired extent.

9. The method of claim 7, wherein the forming cup is a first forming cup and further comprising:

removing the first forming cup from the sealing assembly; and installing a second forming cup in the sealing assembly relative to the light generator.

10. The sealing assembly of claim 1, wherein the sealing assembly is an end effector.

11. The sealing assembly of claim 1, wherein the forming cup is retained within the sealing assembly by holding the base of the forming cup in the forming cup attachment of the sealing assembly.

12. The sealing assembly of claim 11, wherein an opening of the internal cavity faces away from the base of the forming cup.

13. The sealing assembly of claim 11, wherein the base of the forming cup is wider than the body of the forming cup containing the internal cavity.

14. The sealing assembly of claim 11, wherein the forming cup attachment comprises a housing configured to receive gaskets and the forming cup.

15. The sealing assembly of claim 14, wherein a first gasket of the gaskets is positioned between the base of the forming cup and the housing, and wherein a second gasket of the gaskets is positioned between the retainer and the base of the forming cup.

16. The sealing assembly of claim 11, wherein the light housing is configured to protect the light generator from contaminants.

17. The sealing assembly of claim 16, wherein the light housing connects to a further comprising the cooling plate connected to the light generator and a liquid coolant supply system.

18. The sealing assembly of claim 6, wherein the support structures are positioned on a board of the light generator, wherein the support structures are positioned outside of an emissive region of the light generator containing the light emitting diode array, and wherein a diameter of the board is greater than a diameter of the emissive region.

19. A sealing assembly configured to form a sealant coating on a fastener, such that the sealing assembly comprises each of the following components having a common central axis :

a light generator at an end of the sealing assembly connected to a cooling plate configured to connect to a robotic arm and configured to generate a light that comprises a number of characteristics that cures the sealant coating on the fastener;

a light housing configured to: surround the light generator;

receive, at a first end of the light housing, a retainer of the light housing, said retainer of the light housing, configured to include a first quick release connector;

a second end of the light housing configured to interface with the cooling plate to encompass the light generator;

a forming cup that comprises:

a base and a body;

a material substantially transparent to the light generated by the light generator; and a shape configured to direct the light to the sealant coating contained within an internal cavity of the forming cup; and a forming cup attachment located between the forming cup and the light housing;

said forming cup attachment comprises a second quick release connector configured to removably connect to the light housing; and said forming cup attachment configured to retain the forming cup a constant distance from the light generator within the sealing assembly; said retainer of the forming cup attachment configured to hold a portion of the forming cup within the forming cup attachment; and said retainer of the forming cup attachment comprises threads configured to receive a second quick release connector configured to connect the forming cup to the forming cup attachment.

20. The sealing assembly of claim 19 further comprising: the cooling plate connected to a liquid coolant supply system.

21. The sealing assembly of claim 19, wherein the forming cup further comprises at least one of a release layer positioned within the internal cavity, or a reflective coating associated with an angled portion of the forming cup.

22. The sealing assembly of claim 19, wherein the light generator comprises:

a light emitting diode array.

23. The sealing assembly of claim 22, wherein the light emitting diode array has a desired density of packing.

* * * * *